(12) United States Patent
Braun et al.

(10) Patent No.: US 7,424,369 B2
(45) Date of Patent: Sep. 9, 2008

(54) PHYSICAL-CHEMICAL PROPERTY BASED SEQUENCE MOTIFS AND METHODS REGARDING SAME

(75) Inventors: Werner Braun, Friendswood, TX (US); Venkatarajan S. Mathura, Sarasota, FL (US); Catherine H. Schein, Friendswood, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 365 days.

(21) Appl. No.: 10/817,530

(22) Filed: Apr. 2, 2004

(65) Prior Publication Data

US 2005/0043896 A1 Feb. 24, 2005

Related U.S. Application Data

(60) Provisional application No. 60/460,769, filed on Apr. 4, 2003.

(51) Int. Cl.
*G01N 33/48* (2006.01)
(52) U.S. Cl. .......................................... 702/19; 702/20
(58) Field of Classification Search ........................ None
See application file for complete search history.

(56) References Cited

U.S. PATENT DOCUMENTS

| | | | |
|---|---|---|---|
| 5,845,049 A | 12/1998 | Wu | |
| 5,878,373 A | 3/1999 | Cohen et al. | |
| 6,512,981 B1 | 1/2003 | Eisenberg et al. | |

OTHER PUBLICATIONS

Altschul et al., "Grapped BLAST and PSI-BLAST: a new generation of protein database search programs," *Nucleic Acids Res*, 1997;25(17):3389-3402.
Bairoch et al., "The SWISS-PROT protein sequence database and its supplement TrEMBL in 2000," *Nucleic Acids Res*, 2000;28(1):45-48.
Ben-Hur et al., "Remote homology detection: a motif based approach," *Bioinformatics*, 2003;19(Suppl. 1):i26-i33.
Benner et al., "Amino acid substitution during functionally constrained divergent evolution of protein sequences," *Protein Eng.*, 1994;7:1323-1332.
"BLAST." [online]. NCBI Blast.National Institute of Health. [retrieved on Jul. 6, 2004].Retrieved from the Internet:<http:www.ncbi.nlm.nih.gov/BLAST/>;1 pg.
Bowie et al., "A method to identify protein sequences that fold into a known three-dimensional structure," *Science*, 1991;253:164-170.
Brenner et al., "The ASTRAL compendium for protein structure and sequence analysis," *Nucleic Acids Res.*, 2000;28:254-256.
Chandonia et al., "ASTRAL compendium enhancements," *Nucleic Acids Res.*, 2002;30(1):260-263.
Chothia et al., "The relation between the divergence of sequence and structure in proteins," *EMBO J*, 1986;5: 823-826.
"ClustalW." [online]. European Bioinformatics Institute (EMBL-EBI).[retrieved on Jul. 6, 2004]. Retrieved from the Internet:<http://www.ebi.ac.uk/clustalw/>;2 pgs.

Dubchak et al., "Recognition of a protein fold in the context of the SCOP classification," *Proteins*, 1999;35:401-407.
Eddy, S.R., "Profile hidden Markov models," *Bioinformatics*, 1998;14:755-763.
"Emotif Maker." [online]. Biochemistry. Standford University, Standford, CA [retrieved on Jul. 6, 2004].Retrieved from the Internet:<http://fold.stanford.edu/emotif/emotif-maker.html>;2 pgs.
Falquet et al., "The Prosite database, its status in 2002," *Nucleic Acids Res*, 2002;30:235-238.
Gough et al., "SuperFamily: HMMs representing all proteins of known structure. SCOP sequence searches, alignments and genome assignments," *Nucleic Acids Res*, 2002;30: 268-272.
Gribskov et al., "Identification of sequence patterns with profile analysis," *Methods Enzymol*, 1996;266:198-212.
Henikoff et al., "Increased coverage of protein families with the Blocks Database servers," *Nuclic Acids Res*, 2000;28:228-230.
Henikoff et al., "Blocks+: a non-redundant database of protein alignment bloicks derived from multiple compilations," *Bioinformatics*, 1999, 15:471-479.
Henikoff et al., "Protein family classification based on searching a database of blocks," *Genomics*, 1994;19:97-107.
Higgins et al., "Multiple sequence alignment," *Methods Mol Biol.*, 2000;143: 1-18.
Holm et al., "Mapping the protein universe," *Science*, 2000;273:595-602.
Kelley et al., "Enhanced genome annotation using structural profiles in the program 3D-PSSM," *J Mol Biol*, 2000;299: 499-520.
Kostich et al., "Human members of the eukaryotic protein kinase family," *Genome Biol*, 2002;3:43.
Kullback et al., "On information sufficiency," *Ann Math Stat*, 1951;22: 79-86.
Lo Conte et al., "SCOP database in 2002: refinements accommodates structural genomics," *Nucleic Acids Res*, 2002;30: 264-267.
Marcotte et al., "A combined algorithm for genome-wide prediction of protein function," *Nature*, 1999;402:83-86.
Marcotte, E.M., "Computational genetics: finding protein function by nonhomology methods," *Curr Opin. Struct. Biol.*, 2000;10:359-365.
Martelli et al., "A sequence-profile-based HMM for predicting and discriminating beta barrel membrane proteins," *Bioinformatics*, 2002;18: S46-53.
Mathura et al., "Identifying Property Based Sequence Motifs in Protein Families and Superfamilies: Application to DNase I related endonucleases," *Bioinformatics*, 2003;19(11):1381-1390.
Mathura et al., "Automated Generation of Property Based Motifs to Search for Functional Neighbors and to Improve Sequence Alignments," 5th *Meeting on the Critical Assessment of Techniques for Protein Structure Prediction*, CASP5, Asilomar Conference Center, Pacific Grove, CA, Dec. 1-5, 2002: A-178-179.

(Continued)

*Primary Examiner*—Lori A Clow
(74) *Attorney, Agent, or Firm*—Mueting, Raasch & Gebhardt, P.A.

(57) ABSTRACT

A data analysis system, program, and/or method, e.g., a data mining/data exploration method, using physical-chemical property motifs. For example, a sequence database may be searched for identifying segments thereof having physical-chemical properties similar to the physical-chemical property motifs.

22 Claims, 17 Drawing Sheets

OTHER PUBLICATIONS

Mathura et al., "Identifying Property Based Sequence Motifs in Protein Families and Superfamilies: Application to APE," *2002 Bioinformatics Symposium*, Rice University, Houston, TX, Oct. 14-15, 2002: 37.

Mathura et al., "Defining Physical-chemical Properties based motifs specific for members of the APE family of DNA repair proteins," 7th *Structural Biology Symposium*, UTMB, Galveston, TX, May 17-19, 2002:93.

Mathura et al., "Sequence and Structural Analysis of APE 1 Protein Family Using Physical-chemical Properties Based Motifs," *RECOMB, Currents in Computational Moelecular Biology 2002*, Washington, DC.: 191-192.

Mathura et al., "Physical-chemical properties based motifs for annotating protein sequences from genomic data," *Molecular Genomics 2002: Profiling of Gene Expression*, UTMB, Galveston, TX, Apr. 5-7, 2002:35.

Mathura et al., "Quantitative Descriptors for Amino Acids Based on Physico-Chemical Properties using Vector Representation," *Keck 2000 Symposium*, Baylor College of Medicine and Rice University, Houston, TX, Oct. 16-17, 2000: 33.

Mathura et al., "A New Vector Representation of Amino Acids Based on Large Number of Physico-Chemical Properties," *Fifth Annual Structural Biology Symposium*, UTMB, Galveston, TX, May 19-21, 2000: 54.

Mehta et al., "Recognizing very distant sequence relationships among proteins by family profile analysis," *Proteins*, 1999;35:387-400.

Nagano et al., "One fold with many functions: the evolutionary relationships between TIM barrel families based on their sequences, structures and functions," *J Mol Biol*, 2002;321:741-765.

Norin et al., "Structural proteomics: developments in structure-to-function predictions," *Trends Biotechnol.*, 2002;20:79-84.

Overbeek et al., "The use of gene clusters to infer functional coupling," *Proc Natl Acad Sci USA*, Mar. 16, 1999;96(6):2896-2901.

Oezguen et al., "APE1: Identifing Motifs by MASIA and Metalion Position by MD-Simulations," *Keck Center 2001 Annual Research Conference*, Galveston, TX, Sep. 21, 2001:35.

Press et al., "Numerical Recipes in C: The Art of Scientific Computing," 1999, Cambridge University Press, New York.

"Prosite Database of protein families and domains."[online]. Expasy Prosite.[retrieved on Jul. 6, 2004]. Retrieved from the Internet. <http://us.expasy.org/prosite/>;2 pgs.

Rigoutsos et al., "Dictionary-driven protein annotation," *Nucleic Acids Res*, 2002;30:3901-3916.

Rison et al., "Comparison of funcitonal annotation schemes for genomes," *Funct Integr. Genomics*, 2000;1:56-69.

Rychlewski et al., "Comparison of sequence profiles. Strategies for Structural predictions using sequence information," *Protein Sci*, 2000;9:232-241.

Schaffer et al., "IMPALA: matching a protein sequence against a collection of PSI-BLAST-constructed position-specific score matrices," *Bioinformatics*, 1999;16:1000-1011.

Schaffer et al., "Improving the accuracy of PSI-BLAST protein database searches with composition-based statistics and other refinements," *Nucleic Acids Res*, 2000;29:2994-3005.

Schein et al., "Total sequence decomposition distinguishes functional modules, "molegos" in apurinic/apyrimidinic endonucleases," *BMC Bioinformatics*, 2002;3:37.

Schein et al., "Structural and Functional Motifs of Apurinic/Apyrimidinic Endonuclease," *Sealy Center for Molecular Science, Science Forum*, UTMB, Galveston, TX, Mar. 20, 2002: 7.

Schein et al., "Structural and Functional Motifs of Apurinic/Apyrimidinic Endonuclease," *Keystone Symposia Structural Genomics: From Gene Sequence to Function*, Breckenridge, CO, Jan. 5-11, 2002.

Schein et al., "Defining the mode of action of APE1 using MASIA motif searching, MD-simulations and site directed mutagenesis," 6th *Annual Structural Biology Symposium*, UTMB Galveston, TX, May 18-20, 2001: 83.

Truong et al., "Identification and characterization of subfamily-specific signature in a large protein superfamily by a hidden Markov model approach," *BMC Bioinformatics*, 2002;3(1).

Urushihara, H., "Functional genomics of the social amoebae, *Dictyostelium discoideum*," *Mol. Cell*, 2002;13:1-4.

Venkatarajan et al., "New quantitative descriptors of amino acids based on multidimensional scaling of a large number of physical-chemical properties," *J Mol Model*, 2001;7:445-453.

Waterston et al., "On the sequencing of the human genome," *Proc. Natl. Acad. Sci. USA*, 2002;99(6):3712-3716.

Yona et al., "Within the twilight zone: a sensitive profile-profile comparison tool based on information theory," *J Mol Biol.*, 2002;315: 1257-1275.

Zhu et al., "MASIA: recognition of common patterns and properties in multiple aligned protein sequences," *Bioinformatics*, 2000;16:950-951.

Schein et al., "Molego-Based Definition of the Architecture and Specificity of Metal-Binding Sites," *Proteins: Structure, Function, and Bioinformatics*, 2005; 58:200-210.

Schein et al., "Stereophysicochemical variability plots highlight conserved antigenic areas in Flaviviruses," *Virology Journal*, Apr. 2005; 2:40.

Figure 9A

| Motif No. | Query sequence (human APE) | (S1) | (S2) | (S3) | (S4) | 42 APE score ave. ± std. dev | ASTRAL40 ave. ± std. dev |
|---|---|---|---|---|---|---|---|
| 1 | 62 LKICSWNVDGLRA 74 | 0.91* | 0.90* | 0.63* | 0.73* | 0.87 ± 0.05 | 0.56 ± 0.05 |
| 2 | 89 PDILCLQETK 98 | 0.96* | 0.93* | 0.84* | 0.70* | 0.92 ± 0.04 | 0.61 ± 0.07 |
| 3 | 125 KEGYSGVGLLSRQCP 139 | 0.91* | 0.86* | 0.60 | 0.66 | 0.85 ± 0.06 | 0.64 ± 0.05 |
| 4 | 145 GIGDEEHDQEGRVIVAEFDSFVL 169 | 0.94* | 0.77* | 0.71 | 0.81 | 0.84 ± 0.09 | 0.67 ± 0.07 |
| 5 | 171 YVPNA 175 | 0.96* | 0.96* | 0.68 | 0.86 | 0.94 ± 0.06 | 0.68 ± 0.13 |
| 6 | 181 RLEYRQRW 188 | 0.80* | 0.70* | 0.78 | 0.77 | 0.74 ± 0.06 | 0.67 ± 0.05 |
| 7 | 204 PLVLCGDLNVAH 215 | 0.96* | 0.88* | 0.82* | 0.78* | 0.90 ± 0.04 | 0.55 ± 0.08 |
| 8 | 231 GFTPQERQGFGEL 243 | 0.96* | 0.91* | 0.78 | 0.73 | 0.87 ± 0.09 | 0.70 ± 0.07 |
| 9 | 247 VPLADSFR 254 | 0.96* | 0.93* | 0.70 | 0.83 | 0.91 ± 0.08 | 0.74 ± 0.11 |
| 10 | 264 YTFWTYM 270 | 0.86* | 0.77* | 0.61 | 0.70 | 0.84 ± 0.08 | 0.61 ± 0.06 |
| 11 | 274 RSKNVGWRLDYFLLSHSL 291 | 0.92* | 0.89* | 0.56 | 0.64 | 0.90 ± 0.04 | 0.54 ± 0.07 |
| 12 | 306 GSDHCPI 312 | 0.93* | 0.94* | 0.88* | 0.83* | 0.92 ± 0.03 | 0.52 ± 0.09 |

Figure 9B

| PDB[1] | Score in bits (fraction to the highest score) | Motifs found | SCOP[2] | EC[3] | Description |
|---|---|---|---|---|---|
| 1HD7 | 1942 (1.00) | 1,2,3,4,5,6,7,8,9,10,11,12 | d.151.1.1 | 4.2.99.18 | APE |
| 1AKO | 1861 (0.96) | 1,2,3,4,5,7,8,9,10,11,12 | d.151.1.1 | 3.1.11.2 | Exonuclease III |
| 2DNJ | 1094 (0.56) | 2,6,7,12 | d.151.1.1 | 0.0.0.0 | Deoxyribonuclease I |
| 1I9Y | 1056 (0.54) | 1,4,5,6,7,9,12 | d.151.1.2 | 0.0.0.0 | Phosphatidylinositol phosphate Synaptojanin |
| 1B3U | 840 (0.43) | 5,7,9,12 | a.118.1.2 | 0.0.0.0 | Regulatory domain of protein phosphatase |
| 1MDA | 814 (0.42) | 6,9,11,12 | b.69.2.1 | 1.4.99.3 | Methylamine dehydrogenase |
| 1MPY | 797 (0.41) | 7,9,12 | d.32.1.3 | 1.13.11.2 | Catechol 2,3-dioxygenase |
| 1EKM | 792 (0.41) | 6,7,12 | b.30.2.1 | 1.4.3.6 | Copper amine oxidase |
| 1YRG | 737 (0.38) | 2,9,12 | c.10.1.2 | 0.0.0.0 | GTPase RNA1 |
| 1QQ9 | 698 (0.36) | 5,6,12 | c.56.5.4 | 3.4.11.- | Aminopeptidase |

[1] PDB code of the protein
[2] SCOP code and d.151.1 is the DNaseI superfamily code
[3] Enzyme commission classification number

Figure 9C

| PDB[1] | Score in bits (fraction to the highest score) | MOLEGOS found | SCOP[2] | EC[3] | Description |
|---|---|---|---|---|---|
| 1HD7 | 1942 (1.00) | 1,2,3,4,5,6,7,8,9,10,11,12 | d.151.1.1 | 4.2.99.18 | APE (Mn/Mg/Pb) |
| 1AKO | 1831 (0.94) | 1,2,3,5,6,7,8,9,10,11,12 | d.151.1.1 | 3.1.11.2 | Exonuclease III |
| 2DNJ | 1072 (0.55) | 1,2,5,6,7,9,10,12 | d.151.1.1 | 3.1.21.1 | Deoxyribonuclease I |
| 1I9Y | 971 (0.50) | 1,2,5,6,7,9,10,12 | d.151.1.2 | | Phosphatidylinositol phosphate Synaptojanin |
| 1QQ9 | 698 (0.36) | 5,6,9,10,12 | c.56.5.4 | 3.4.11.- | Aminopeptidase (Zn, Ca) |
| 1ATL | 633 (0.33) | 5,6,9,10,12 | d.92.1.9 | 3.4.24.42 | Snake venom metalloprotease (Zn, Ca) |
| 1D09 | 619 (0.32) | 5,9,12 | d.58.2.1 | 2.1.3.2 | Aspartate carbamoyltransferase (Zn) |
| 1D2N | 613 (0.32) | 5,6,8,9,12 | c.37.1.13 | | N-ethylmalemide of sensitive fusion protein (Mg) |
| 1D0B | 579 (0.30) | 2,5,9,12 | c.10.2.1 | | InternalinB LRR domain (Ca) |
| 1EEM | 571 (0.29) | 5,6,8,12 | a.45.1.1 | | Glutathione S-transferase |

[1] PDB code of the protein
[2] SCOP code and d.151.1 is the DNaseI superfamily code
[3] Enzyme commission classification number

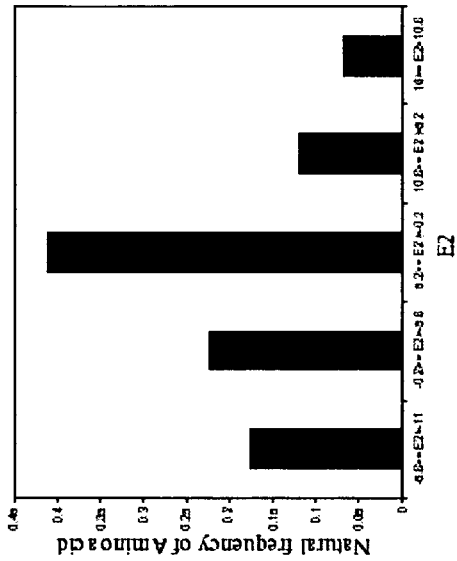
Figure 10 - E2
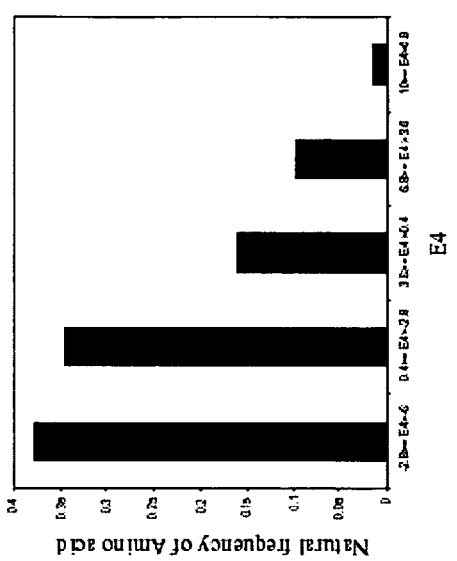
Figure 10 - E4
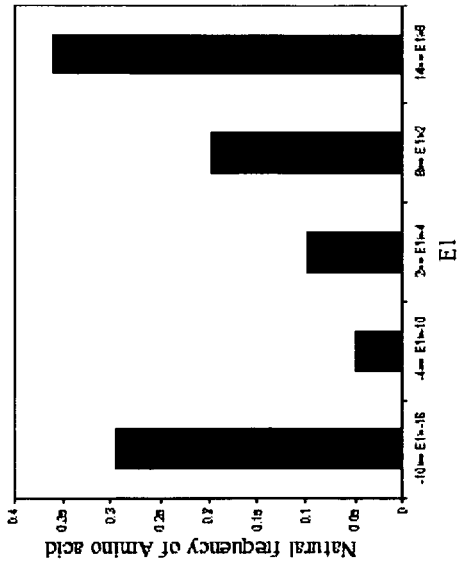
Figure 10 - E1
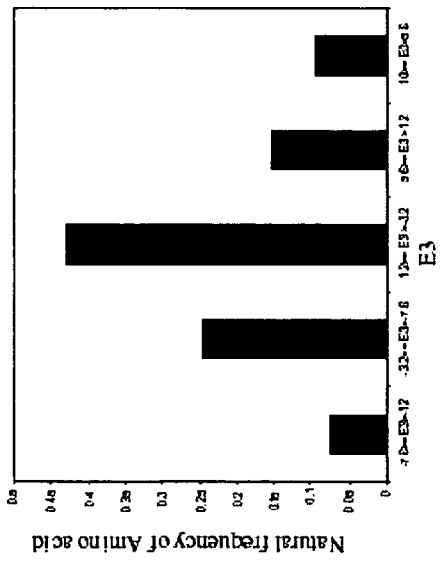
Figure 10 - E3

Figure 11

| SEQ ID NO: 1 | P | D | I | L | C | L | Q | E | T | K |
|---|---|---|---|---|---|---|---|---|---|---|
| E1 | * | + | - | - | - | - | + | + | * | * |
| E2 | * | - | * | * | * | * | - | - | * | - |
| E3 | + | * | * | * | * | * | * | - | * | * |
| E4 | * | + | * | * | + | * | + | + | * | - |
| E5 | * | + | * | * | * | * | - | + | * | - |

Figure 13

```
                                      1
Seq ID No: 2 1bix    ........LYEDPPDQKTSPSGKPAT LKICSWNVDGLRA W......IKKKGLDWVKE.EA
Seq ID No: 3 1ako    ........................  MKFVSFNINGLRA R......P..HQLEAIVEkHQ
Seq ID No: 4 3dni    ........................  LKIAAFNIRTFGE tkmsnatLASYIVRIVR...R
Seq ID No: 5 1i9yA   ydpiheyvnhelrkrenefseHKNVK IFVASYNLNG..C S......ATTK.LENWLF.Pe
                                      2
             1bix    P......DILCLQETK ....CSENKL.P..AELQEL..........PGLSHQYWS.APSD
             1ako    P......DVIGLQETK ....VHDDMF.P.1EEVAKL..........G..YNVFYH.G...
             3dni    Y......DIVLIQEVR ....DSHLVAvG..KLLDYL.....nqddpNTYH.YVVSePLGR
             1i9yA   ntpladiYVVGFQEIV qltsADPAkrreweSCVKRLlngkctsgpgYVQLRSGQL.V...

3                          4
             1bix    KEGYSGVGLLSR...QCP........LKVSYGIGDE....EHDQE.GRVIVAEFD.....
             1ako    QKGHYGVALLTK...ETP........IAVRRGFPGD.....DEEAqRRIIMAEIP...sl
             3dni    nSYKERYLFLFRpnkVSV........LDTYQ.YDDGccgnDSFSR..EPAVVKFSshstk
             1i9yA   .....GTALMIF...CkesclpsiknVEGTVKK.......tGLGN.KGAVAIRFD...ye 5               6
             1bix    ..SFVLVTAYVPNAGRGLV..RLEYRQRWDEAFRKFLKG.......LA...S.RK.PLVL
             1ako    1gNVTVINGYFPQGESRDHpiKFPAKAQFYQNLQNYLET.......EL...KrDN.PVLI
             3dni    vkEFAIVALHSAPS..........DAVAEINSLYDVYLD.......VQqkwH.LN.DVMI
             1i9yA   dtGLCFITSHLAAGY........TNYDERDHDYRTIASglrfrrgrSI...F.NHdYVVW 7                                     8
             1bix    CGDLNVAHEEIDLRN....PKGNK..KNAGFTPQ.................EROGF
             1ako    MGDMNISPTDLDIGIgeenRKRWLrtGKCSFLPE.................EREWM
             3dni    MGDFNAD.....................CSYVTSS................QWSS.
             1i9yA   FGDFNY..................RISLtyeevvpciaqgklsylfeydqLNKQM 9                10                11
             1bix    G..ELLQAVPLADSFRHLYPNTPYAYTFWTY..MMNARSKNV...GWRLDYFLLSHS.LL
             1ako    D..RLMSW.GLVDTFRHANPQTADRFSWFDY..RSKGFDDNR...GLRIDLLLASQP.LA
             3dni    I..RLRTSSTFQWLIP......dSADTTAT..........ST...NCAYDRIVVAGS1LQ
             1i9yA   LtgKVFP..FFSELPI......tfPPTYKFDigTDIYDTSdkhrvPAWTDRILYRGE.L.

12
             1bix    PALC..DSKIRSKA...........L....GSDHCPI TLYLAL................
             1ako    ECCV..ETGIDYEI...........Rsmek PSDHAPV WATFRR................
             3dni    SSVVpgSAAPFDFQaayglsnemalA....ISDHYPV EVTLT.................
             1i9yA   .VPH..SYQSV.PL...........Y....YSDHRPI YATYEAnivkvdrekkkilfeel 1bix    ...........
             1ako    ...........
             3dni    ...........
             1i9yA   ynqrkqevrdasq
```

US 7,424,369 B2

PHYSICAL-CHEMICAL PROPERTY BASED SEQUENCE MOTIFS AND METHODS REGARDING SAME

CROSS-REFERENCE TO RELATED APPLICATIONS

This application claims the benefit of U.S. Provisional Application No. 60/460,769, entitled "PHYSICAL-CHEMICAL PROPERTY BASED SEQUENCE MOTIFS AND METHODS REGARDING SAME," filed 4 Apr. 2003, wherein such document is incorporated herein by reference.

GOVERNMENT FUNDING

The present invention was made with government support under Grant No. DE-FG03-00ER63041 and DE-FG02-04ER63826, awarded by the Department of Energy. The Government has certain rights in this invention.

BACKGROUND OF THE INVENTION

The present invention relates generally to the analysis of sequence data. More particularly, the present invention pertains to defining physical-chemical property (PCP) based sequence motifs common to a family of related proteins and/or the use thereof in analysis of sequence data (e.g., DNA, RNA, amino acids), such as, for example, searching genomic sequence databases to identify homologues of the family of proteins.

With improvement of technology, the amount of sequence data available for analysis is accumulating very quickly. The ability to analyze such sequence data depends significantly on the development of advanced computational tools for rapid and accurate annotation of genomic sequences as to the probable structure and function of the proteins they encode.

As such, one of the most challenging goals of genome sequencing projects is to functionally annotate novel gene products (Kelley, et al., 2000 and Rison, et al., 2000). A sequence can be recognized as a homologue of a known protein if the pair-wise sequence identity/similarity exceeds a statistically derived threshold (e.g., more than 30% sequence identity or an E-value less than 0.001) (Chothia, et al., 1986). These global criteria identify only a small fraction of proteins known to be functionally related, as amino acids patterns are differently conserved.

Determining the similarity of sequences in databases to that of proteins of known function has been one of the most direct computational ways of deciphering codes that connect molecular sequences of protein structure and function. There are various algorithms and software available for sequence database searching and sequence analysis which, for example, may provide for comparisons between query sequences and sequence data (e.g., sequence data in a molecular database). Sequence profile searches (Bowie, et al., 1991; Gribskov, et al., 1996; Mehta, et al., 1999; Rychlewski, et al., 2000; and Schaffer, et al., 1999) and Hidden Markov Models (Eddy, S. R., 1998) generate position specific fingerprints of the amino acid sequences in protein families and can identify distantly related proteins. However, the optimal choice of parameters for high sensitivity/specificity depends on the expert user. A further complication is that enzymes often combine functional elements to create a specific catalytic center. These elements, due to crossover events, may not occur in the same linear fashion in the sequence of related proteins and are not found with global profiles.

Analytical tools that use statistically derived matrices based on allowed substitution of amino acids, are not designed to detect conservation of physical-chemical properties. For example, such tools include those available under the trademark or the trade designation of FASTA, PSI-BLAST, or BLOCKS, such as described in Pearson W., Rapid and sensitive sequence comparison with FASTP and FASTA, *Methods in Enzymology*, 1990, 183:63-98; Schaffer et al., Improving the accuracy of PSI-BLAST protein database searches with composition-based statistics and other refinements, *Nucleic Acids Res*, 2001, 29(14): 2994-3005; Schaffer et al., IMPALA: matching a protein sequence against a collection of PSI-BLAST constructed position-specific score matrices, *Bioinformatics*, 1999, 15: 1000-1011; Altschul et al., Gapped BLAST and PSI-BLAST: a new generation of protein database search programs, *Nucleic Acids Res*, 1997, 25(17): 3389-3402; and Henikoff et al., Increased converage of protein families with the blocks database servers, *Nucleic Acids Res*, 2000, 28: 228-230.

Other database searching tools that are based on information derived from a family of related proteins include, for example, a screening for motif patterns such as described in U.S. Pat. No. 5,845,049, to Wu, issued Dec. 1, 1998, and entitled "Neural network system with n-gram term waiting method for molecular sequence classification and motif identification." Wu describes a method using a neural network that is trained for extraction of sequence motifs. Further, for example, other analysis processes may use other fold recognition tools (e.g., U.S. Pat. No. 6,512,981 B1, to Eisenberg, et al., issued Jan. 28, 2003, entitled "Protein fold recognition using sequence-derived predictions"). Eisenberg et al. describes a method that relies, to a large extent, on the knowledge of 3D protein structures for fold assignment.

Most genome sequencing projects represent their results in databases including large collections of sequences. As such, a critical step in the selection of potential drug targets among novel gene products is functional annotation. Global sequence similarity criteria can only identify a small fraction of proteins known to be functionally related, as amino acid patterns are not uniformly conserved and it is not known what physical-chemical properties are conserved. The large number of potential physical-chemical properties makes it difficult to know 'a priori' which of these properties and at what positions in the protein sequence these properties are conserved. A process for deriving five descriptors for amino acids using 237 physical-chemical properties is described in the article by Venkatarajan, M. S. and Braun, W. (2001), entitled "New quantitative descriptors of amino acids based on multidimensional scaling of a large number of physical-chemical properties," *J. Mol. Model.*, 7, pp 445-453.

The available or described sequence data analysis methods range from very sensitive, but computationally intensive algorithms, to relatively rapid, but less sensitive analysis methods. As such, although various analysis tools are available, there is still a need for the development of database search methods that are relatively rapid and also relatively more sensitive. Further, there is always a need for processes that use functional information (e.g., physical-chemical property information) to effectively extract useful information from sequence data being searched.

REFERENCES

The following references (many of which are referred to above) to the extent that they provide exemplary procedural or other details supplementary to those set forth herein, are specifically incorporated herein by reference. Such references are not to be considered prior art to the present invention merely by such references being a part of this list.

Altschul, et al. (1997) Gapped BLAST and PSI-BLAST: a new generation of protein database search programs, *Nucleic Acids Res.*, 25, 3389-3402.

Bairoch, et al. (2000) The SWISS-PROT protein sequence database and its supplement TrEMBL in 2000, *Nucleic Acids Res.*, 28, 45-48.

Benner, et al. (1994) Amino acid substitution during functionally constrained divergent evolution of protein sequences, *Protein Eng.*, 7, 1323-1332.

Bowie, et al. (1991) A method to identify protein sequences that fold into a known three-dimensional structure, *Science*, 253, 164-170.

Brenner, et al. (2000) The ASTRAL compendium for protein structure and sequence analysis, *Nucleic Acids Res.*, 28, 254-256.

Chandonia, et al. (2002) ASTRAL compendium enhancements, *Nucleic Acids Res.*, 30, 260-263.

Chothia, et al. (1986) The relation between the divergence of sequence and structure in proteins, *EMBO J.*, 5, 823-826.

Dubchak, et al. (1999) Recognition of a protein fold in the context of the SCOP classification, *Proteins*, 35, 401-407.

Eddy, S. R. (1998) Profile hidden Markov models, *Bioinformatics*, 14, 755-763.

Falquet, et al. (2002) The PROSITE database, its status in 2002, *Nucleic Acids Res.*, 30, 235-238.

Gough, et al. (2002) SUPERFAMILY: HMMs representing all proteins of known structure. SCOP sequence searches, alignments and genome assignments, *Nucleic Acids Res.*, 30, 268-272.

Gribskov, et al. (1996) Identification of sequence patterns with profile analysis, *Methods Enzymol*, 266, 198-212.

Henikoff, et al. (2000) Increased coverage of protein families with the Blocks Database servers, *Nucleic Acids Res.*, 28, 228-230.

Henikoff, et al. (1999) Blocks+: a non-redundant database of protein alignment blocks derived from multiple compilations, *Bioinformatics*, 15, 471-479.

Henikoff, et al. (1994) Protein family classification based on searching a database of blocks, *Genomics*, 19, 97-107.

Higgins, et al. (2000) Multiple sequence alignment, *Methods Mol. Biol.*, 143, 1-18.

Holm, et al. (1996) Mapping the protein universe, *Science*, 273, 595-602.

Kelley, et al. (2000) Enhanced genome annotation using structural profiles in the program 3D-PSSM, *J. Mol. Biol.*, 299, 499-520.

Kostich, et al. (2002) Human members of the eukaryotic protein kinase family, *Genome Biol.*, 3, 43.

Kullback, et al. (1951) On information sufficiency, *Ann. Math. Stat.*, 22, 79-86.

Lo Conte, et al. (2002) SCOP database in 2002: refinements accommodate structural genomics, *Nucleic Acids Res.*, 30, 264-267.

Marcotte, et al. (1999) A combined algorithm for genome-wide prediction of protein function, *Nature*, 402, 83-86.

Marcotte, E. M. (2000) Computational genetics: finding protein function by nonhomology methods, *Curr. Opin. Struct. Biol.*, 10, 359-365.

Martelli, et al. (2002) A sequence-profile-based HMM for predicting and discriminating beta barrel membrane proteins, *Bioinformatics*, 18, S46-53.

Mehta, et al. (1999) Recognizing very distant sequence relationships among proteins by family profile analysis, *Proteins*, 35, 387-400.

Nagano, et al. (2002) One fold with many functions: the evolutionary relationships between TIM barrel families based on their sequences, structures and functions, *J. Mol. Biol.*, 321, 741-765.

Norin, et al. (2002) Structural proteomics: developments in structure-to-function predictions, *Trends Biotechnol.*, 20, 79-84.

Overbeek, et al. (1999) The use of gene clusters to infer functional coupling, *Proc Natl Acad Sci USA*, 96, 2896-2901.

Rigoutsos, et al. (2002) Dictionary-driven protein annotation, *Nucleic Acids Res.*, 30, 3901-3916.

Rison, et al. (2000) Comparison of functional annotation schemes for genomes, *Funct. Integr. Genomics*, 1, 56-69.

Rychlewski, et al. (2000) Comparison of sequence profiles. Strategies for structural predictions using sequence information, *Protein Sci.*, 9, 232-241.

Schaffer, et al. (1999) IMPALA: matching a protein sequence against a collection of PSI-BLAST-constructed position-specific score matrices, *Bioinformatics*, 16, 488-189.

Schaffer, et al. (2001) Improving the accuracy of PSI-BLAST protein database searches with composition-based statistics and other refinements, *Nucleic Acids Res.*, 29, 2994-3005.

Schein, et al. (2002) Total sequence decomposition distinguishes functional modules, "molegos" in apurinic/apyrimidinic endonucleases, *BMC Bioinformatics*, 3, 37.

Urushihara, H. (2002) Functional genomics of the social amoebae, Dictyostelium discoideum, *Mol. Cell*, 13, 1-4.

Venkatarajan, et al. (2001) New quantitative descriptors of amino acids based on multidimensional scaling of a large number of physical-chemical properties, *J. Mol. Model.*, 7, 445-453.

Waterston, et al. (2002) On the sequencing of the human genome, *Proc. Natl. Acad. Sci. USA*, 99, 3712-3716.

Yona, et al. (2002) Within the twilight zone: a sensitive profile-profile comparison tool based on information theory, *J. Mol. Biol.*, 315, 1257-1275.

Zhu, et al. (2000) MASIA: recognition of common patterns and properties in multiple aligned protein sequences, *Bioinformatics*, 16, 950-951.

SUMMARY OF THE INVENTION

Generally, the present invention includes one or more of several processes or programs (or systems including such programs). For example, the present invention may be considered to include multiple (e.g., in one embodiment, three) processes or programs that may be implemented alone or in combination. Further, the output of one process may be used as an input by another program described herein or any other program that may operate on the input, the input to the process described herein may be receive from an output of another process, or the multiple processes may be used in any other effective combination.

For example, where the present invention is considered to include three processes or programs, a first program or process is operable to generate physical-chemical property (PCP) motifs from aligned sequences (e.g., an input multiple sequence alignment that can be obtained by various known methods).

A second program or process, for example, uses a matrix of values that define the PCP motifs, calculated by the first program or process, to search, in an automatic fashion, for related segments of protein sequences in a sequence database. For example, a positional scoring function based on related standard deviation and relative entropy values determined for positions of the initial multiple sequence alignment may be used. Thereafter, for example, the second program or process may select, for each protein in the sequence database, a highest scoring segment (e.g., such data may be stored for use in further processes or programs).

A third program or process may, for example, be used to analyze the data from the second process or program and determine which proteins (e.g., a ranking of such proteins) most resemble (e.g., in terms of PCP characteristics) the original aligned sequences (e.g., a family of related sequences). For example, the third program may use a Bayesian scoring function to perform such ranking of the proteins.

Further, additional related processes may incorporate the use of structural similarity algorithms. For example, after the above three programs detect significant homologues according to purely sequence criteria, and when structures are available, a process may calculate the segmental root-mean-square deviation (RMSD) between structures associated with the PCP query motif of the aligned sequences and those of the detected sequence segments of the proteins identified in the searched sequence database. The proteins may then be ranked according to overall structural similarity, or according to two criteria, similarity in physical-chemical properties and their overall structural similarity.

In one method of the present invention for use in sequence data analysis, the method includes providing a multiple sequence alignment of a plurality of sequences, wherein the multiple sequence alignment includes a column of aligned amino acids and/or gaps for each horizontal position of the multiple sequence alignment. Further, the method includes providing a plurality of numerical physical-chemical property (PCP) descriptors for each amino acid based on a plurality of physical-chemical properties thereof. Each of the plurality of numerical PCP descriptors corresponds to one of "N" eigenvectors used in defining the amino acids in terms of physical-chemical properties. Each amino acid in the multiple sequence alignment is quantitatively described in terms of the plurality of PCP descriptors as a series of "N" eigenvectors resulting in "N" PCP described sequence alignments, wherein each PCP described sequence alignment corresponds to and is defined with numerical PCP descriptors which correspond to one of the "N" eigenvectors, and further wherein each PCP described sequence alignment includes a plurality of columns corresponding to the columns of the multiple sequence alignment. Each of the PCP described sequence alignments is analyzed, on a column by column basis, to generate conservation property data for each column. The conservation property data for each column includes an average value for the numerical PCP descriptors in the column and a standard deviation associated with the average value, and a relative entropy value for the column. The conservation property data for each of the PCP described sequence alignments is analyzed to detect consecutive horizontal positions of the multiple sequence alignment where the physical-chemical properties are conserved based on the relative entropy determined for each column. Thereafter, the method further defines one or more PCP motifs in the multiple sequence alignment based at least on the detection of consecutive horizontal positions of the multiple sequence alignment where the physical-chemical properties are conserved according to at least one eigenvector.

In one embodiment of the method, analyzing the conservation property data for each of the PCP described sequence alignments includes analyzing the conservation property data for each of the PCP described sequence alignments to detect consecutive horizontal positions where the relative entropy satisfies a predetermined limit.

In another embodiment of the method, defining one or more PCP motifs in the multiple sequence alignment further includes using user specified gap and minimum length limits to define the one or more PCP motifs, wherein each PCP motif comprises a plurality of consecutive horizontal positions in the multiple sequence alignment.

Yet further, in another embodiment of the method, the method includes using the one or more PCP motifs to search a sequence database for related sequence segments having PCP characteristics similar to one or more of the PCP motifs (e.g., defining each of the PCP motifs as a series of PCP motif profile matrices, wherein each PCP motif profile matrix of the series corresponds to one of the "N" eigenvectors, and further wherein values for each PCP motif profile matrix comprise an average value of the numerical PCP descriptors in the column at each horizontal position of the PCP motif and a standard deviation associated with the average value, and a relative entropy value for each horizontal position of the PCP motif).

In another embodiment, using the one or more PCP motifs to search a sequence database for related sequence segments includes converting each of one or more sequences of the sequence database to a searchable form using the numerical PCP descriptors, using a positional scoring function to match values of the series of PCP motif profile matrices defined for each PCP motif to segments of each of the searchable matrices resulting in scored segments, and selecting at least one scored segment for each of the searchable matrices as being a best match to each PCP motif based on results of the positional scoring function. Thereafter, the selected scored segments may be used for ranking the plurality of proteins of the database according to which protein has PCP characteristics that are the closest to the plurality of sequences used to provide the multiple sequence alignment, for example, based on application of a Bayesian scoring function and/or based on structural similarity.

A computer program for use in conjunction with a processing apparatus to analyze sequence data is also provided. The computer program is operable when used with the processing apparatus to recognize a multiple sequence alignment of a plurality of sequences, wherein the multiple sequence alignment comprises a column of aligned amino acids and/or gaps for each horizontal position of the multiple sequence alignment. Further, the program is operable to recognize a plurality of numerical physical-chemical property (PCP) descriptors for each amino acid based on a plurality of physical-chemical properties thereof, wherein each of the plurality of numerical PCP descriptors corresponds to one of "N" eigenvectors used in defining the amino acids in terms of physical-chemical properties. Each amino acid in the multiple sequence alignment can be quantitatively described using the program in terms of the plurality of PCP descriptors as a series of "N" eigenvectors resulting in "N" PCP described sequence alignments. Each PCP described sequence alignment corresponds to and is defined with numerical PCP descriptors which correspond to one of the "N" eigenvectors. Further, each PCP described sequence alignment comprises a plurality of columns corresponding to the columns of the multiple sequence alignment. The computer apparatus is further operable to analyze each of the PCP described sequence alignments, on a column by column basis, to generate conservation property data for each column. The conservation property data for each column includes an average value for the numerical PCP descriptors in the column and a standard deviation associated with the average value, and a relative entropy value for the column. With further use of the program, the conservation property data is analyzed for each of the PCP described sequence alignments to detect consecutive horizontal positions of the multiple sequence alignment where the physical-chemical properties are conserved based on the relative entropy determined for each column and one or more PCP motifs in the multiple sequence alignment are defined based at least on the detection of consecutive horizontal positions of the multiple sequence alignment where the physical-chemical properties are conserved according to at least one eigenvector.

The computer program is further operable to carry out the various process steps described in one or more of the embodiments described herein.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

BRIEF DESCRIPTION OF THE DRAWINGS

FIGS. 9A-9C show tables of information for use in describing one example of the use of an analysis process according to the present invention. The sequence identification numbers for motif numbers 1-12 are as follows: motif number 1, SEQ ID NO:6; motif number 2, SEQ ID NO:7; motif number 3, SEQ ID NO:8; motif number 4, SEQ ID NO:9; motif number 5, SEQ ID NO:10; motif number 6, SEQ ID NO:11; motif number 7, SEQ ID NO:12; motif number 8, SEQ ID NO:13; motif number 9, SEQ ID NO:14; motif number 10, SEQ ID NO:15; motif number 11, SEQ ID NO:16; motif number 12, SEQ ID NO:17.

FIGS. 10-E1 to 10-E4 show illustrations of the distribution of the values for each vector for the naturally occurring amino acids for use in describing one example of the use of an analysis process, according to the present invention. The frequency of occurrence of each amino acid in SWISSPROT (release 40) was used.

FIG. 11 shows one illustration of a qualitative representation of a motif 2 (from FIG. 9A) for use in describing one example of the use of an analysis process according to the present invention. The magnitude of an eigenvector is shown as a positive or negative symbol depending on the average value at that position in the multiple alignment. A '*' indicates the relative entropy is less than 1.25 and the position will not be scored.

FIG. 13 shows one illustration of a structure-based FSSP/DALI alignment of DNase-I family sequences, with motifs defined for the APE family underlined, for use in describing one example of the use of an analysis process according to the present invention. Motif areas that are structurally equivalent (as defined by DALI) are boxed.

DETAILED DESCRIPTION OF THE EMBODIMENTS

The present invention shall generally be described with reference to FIGS. 1 and 2. A more detailed description of one or more further embodiments of the present invention shall be described with reference to FIGS. 3-8. Thereafter, an example using a data analysis process according to the present invention shall be described with further reference to FIGS. 9-14.

Figure 1:
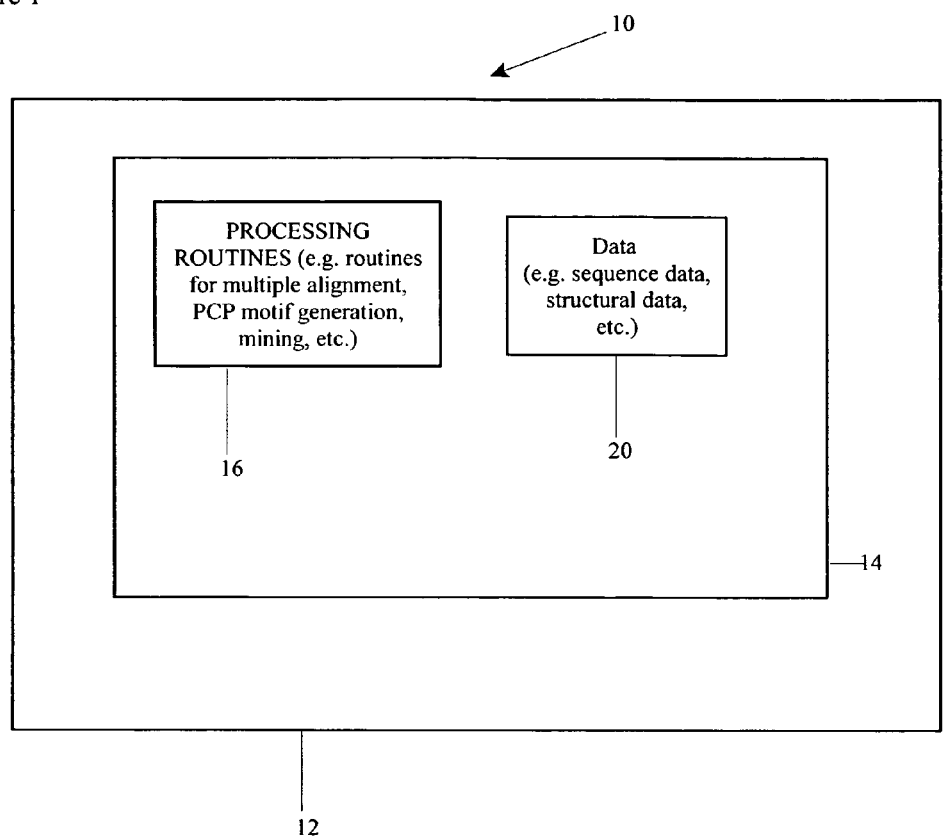
FIG. 1 shows a general block diagram of a general illustrative data processing system for use in analyzing a sequence database according to the present invention.

FIG. 1 shows a data analysis system 10 including a processing apparatus 12 along with associated data storage 14. Data storage 14 allows for access to processing programs or routines 16 and one or more other types of data 20 that may be employed to carry out the illustrative sequence data analysis method 30 as shown generally in the block diagram of FIG. 2.

For example, processing programs or routines 16 may include programs or routines for performing multiple alignment of sequences, physical-chemical property (PCP) based motif generation, data mining, or any other processing required to implement one or more embodiments of the present invention as described herein. Data 20 may include, for example, a sequence database, structural data associated with sequence information, results from one or more processing programs or routines employed according to the present invention, or any other data that is necessary for carrying out the one or more processes described herein.

As used herein, a protein sequence, also referred to herein solely as a sequence, refers to an order of the amino acids (each amino acid represented by a one letter code) in a protein (i.e., a protein molecule).

As used herein, a sequence database refers to any list of one or more sequences in a one letter code form that is in a format readable to a program or processing system. Examples of sequence databases include, for example, SwissProt, RefSeq, PIR, PRF, and PDB or user assembled specific lists of sequences. Further, whenever reference is made to a single sequence database, such a reference also includes a plurality of sequence databases as well. A sequence database also includes translations of nucleotide sequences in, for example, SwissProt (e.g., TrEMBL), GenBank and RefSeq. Such translations can include translations of annotated protein coding regions, and 6 frame translations, i.e., 3 reading frames from the forward nucleotide strand and 3 reading frames from the complementary nucleotide strand.

As used herein, a multiple sequence alignment refers to an alignment of a plurality of sequences with gaps inserted in the sequences to optimize alignment (e.g., to optimize alignment of residues with common structural positions in the same column of the multiple alignment). The alignment is preferably in a format readable to a program or processing system. As such, the multiple sequence alignment includes columns of aligned amino acids and/or gaps for each of a plurality of horizontal positions of the multiple sequence alignment (see, for example, the columns for each horizontal position in the alignment shown in FIG. 13).

As used herein, a sequence segment, also referred to herein solely as a segment, refers to a portion of a sequence (i.e., sometimes also referred to as a sequence fragment).

As used herein, a PCP motif refers to a plurality of columns of the multiple sequence alignment at consecutive horizontal positions thereof determined as described herein based on at least the conservation of PCP characteristics.

In one or more embodiments of the present invention, the data analysis system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein is applied to input data to perform functionality described herein and generate desired output information. The output information may be applied as input to one or more other devices and/or processes as described herein or as would be applied in a known fashion.

The program used to implement the present invention may be provided using any programmable language, e.g., a high level procedural and/or object orientated programming language, that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein.

Likewise, the data analysis system 10 may be configured at a remote site (e.g., an application server) that allows access by one or more users via a remote computer apparatus (e.g., via a web browser), and allows a user to employ the functionality according to the present invention (e.g., user accesses a graphical user interface associated with the program to search a sequence data base, such as a public database).

The processing apparatus 12, may be, for example, any fixed or mobile computer system (e.g., a personal computer or mini computer). The exact configuration of the computing apparatus is not limiting and essentially any device capable of providing suitable computing capabilities may be used according to the present invention. Further, various peripheral devices, such as a computer display, mouse, keyboard, memory, printer, etc., are contemplated to be used in combination with processing apparatus 12 of the data analysis system 14.

In view of the above, it will be readily apparent that the functionality as described in one or more embodiments according to the present invention may be implemented in any manner as would be known to one skilled in the art. As such, the computer language, the computer system, or any other software/hardware which is to be used to implement the present invention shall not be limiting on the scope of the processes or programs (e.g., the functionality provided by such processes or programs) described herein.

One will recognize that a graphical user interface, is used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits or other pertinent information.

Figure 2:
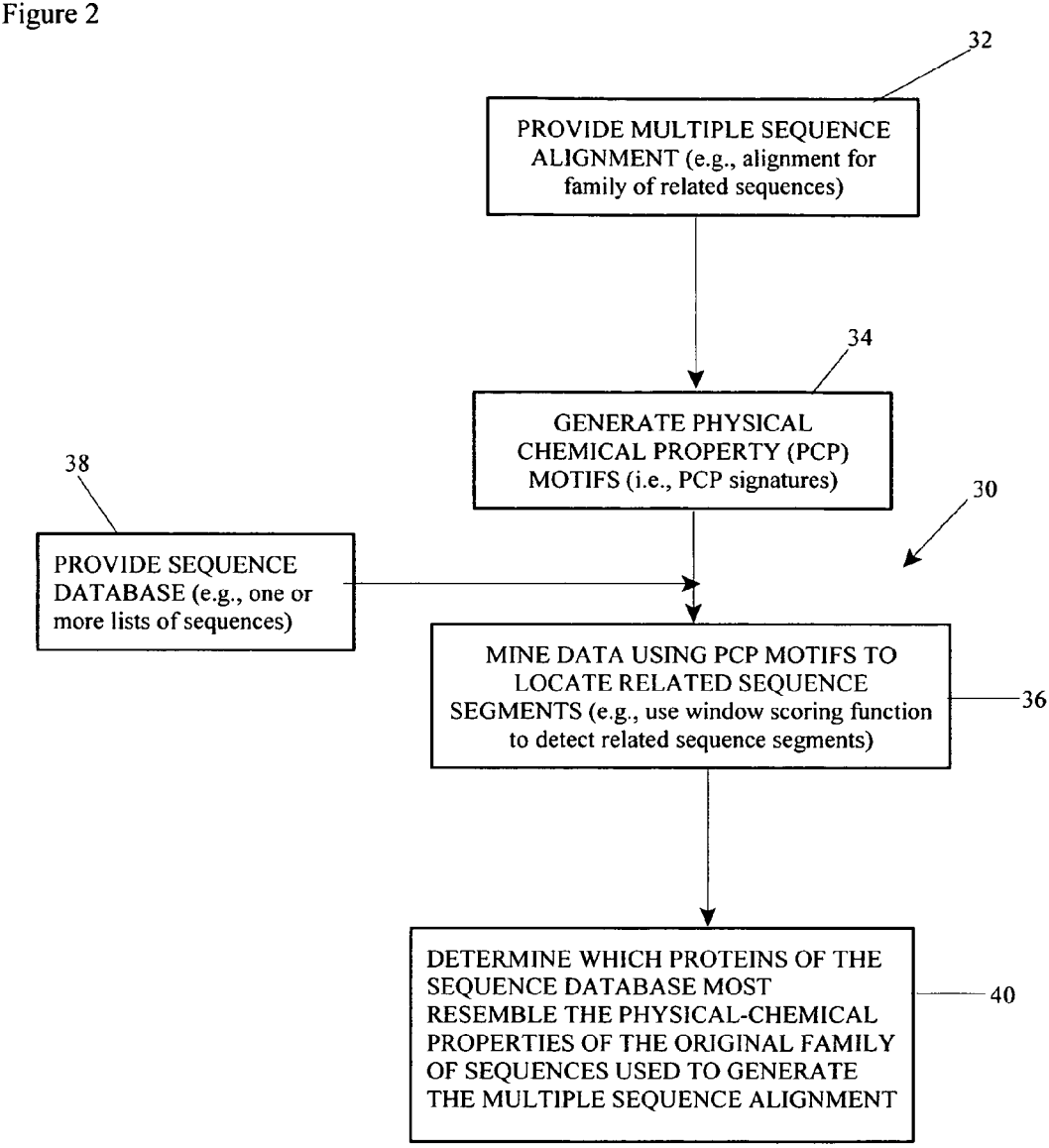
FIG. 2 shows a general block diagram of a general illustrative sequence data analysis process according to the present invention.

FIG. 2 shows a general block diagram of the illustrative generalized sequence data analysis method 30 according to the present invention. One will recognize that one or more of the blocks of functionality described therein may be carried out using one or more programs or routines. Further, certain of the functional blocks may be optional according to one more embodiments of the present invention.

Generally, the sequence data analysis method 30 includes providing the multiple sequence alignment (e.g., providing a multiple sequence alignment for a family of related sequences (block 32)). PCP motifs, e.g., PCP signatures, are then generated for the multiple sequence alignment (block 34) using multidimensional numerical PCP descriptors provided for each amino acid based on the physical-chemical properties of each amino acid. Such PCP motifs may then be used to mine a sequence database to locate related sequence segments (block 36) in a sequence database (block 38).

For example, such data mining may use a positional scoring function to detect related sequence segments of protein sequences of the sequence database. Thereafter, with use of information resulting from the data mining (block 36), one or more processes may be employed to rank the proteins associated with such related segments according to the proteins' resemblance to the PCP characteristics of the family of sequences used to generate the multiple sequence alignment (block 40).

In general, and as will be further described herein, the present invention uses all the information in a multiple sequence alignment to identify common properties of the family of proteins used to generate the multiple sequence alignment. Thereafter, a user may use such identified properties to identify other proteins (e.g., from those proteins defined in a sequence database) that would fit into this family of proteins used to provide the multiple sequence alignment.

Further, and generally, the present invention is based on the conservation of physical-chemical properties of amino acids. The sequence data analysis method 30 provides a procedure in which each amino acid has been represented as a vector in a high-dimensional space determined by a plurality of different physical-chemical properties (e.g., a space determined by 237 different physical-chemical properties). By applying multidimensional scaling, the vector in high-dimensional space may be reduced into N-dimensions without losing information. For example, and as which will be described herein, in one embodiment, multidimensional scaling can reduce the vector in high-dimensional space into five dimensions without losing information. The properties of each amino acid in the reduced space can thus be described by five quantitative descriptors. Conservation of the physical-chemical properties may be reflected by the conservation of these descriptors.

Using a multiple sequence alignment of a plurality of sequences, the motif generating algorithm (block 34) takes the multiple alignment (block 32) and scores for conservation of the properties at each horizontal position of the multiple sequence alignment. For each position, the distribution of the values of the descriptors compared to natural distribution thereof can be expressed by the relative entropy. The magnitude of conservation can be measured as an average of the vectors at the horizontal position (e.g., an average of PCP descriptors for the amino acids in the column at the horizontal position). Using empirical rules, the present invention determines PCP motifs for the multiple sequence alignment. Each horizontal position in the PCP motif has a profile that includes average values for the descriptors and associated standard deviations, and further includes the relative entropies for the descriptors.

A positional scoring function may then be used to score the fit of a PCP profile matrix (e.g., the numerical and probabilistic expression of a PCP motif) to a given sequence in a sliding window to detect segments in a given sequence as data mining of a searchable sequence database is performed to locate related sequence segments (block 36). Thereafter, one or more other scoring functions (e.g., Bayesian scoring function) may be used to determine which of a plurality of proteins of the searchable sequence database most resembles the family of proteins used to generate the multiple sequence alignment from which the PCP motifs are determined.

In other words, conservation in terms of these physical-chemical property eigenvectors in the multi-sequence alignment assists in identifying subtle signatures even among highly diverged protein family members. Such PCP motifs that are conserved in the physical-chemical properties in aligned protein sequences are important for biological function. The PCP motifs generated based on such conservation of the physical-chemical properties can be used to identify functionally related proteins in a sequence database which may have low sequence similarity. Sequence patterns based on conservation within the amino acid alphabet, as reflected in statistically derived substitution matrices, might not be sensitive enough to detect such subtle conservation of physical-chemical properties.

The superiority of the novel method according to the present invention when compared to current methods for determining sequence similarity is evidenced by identifying distant homologues of the human DNA repair enzyme, apurinic/apyrimidinic endonuclease 1 (APE1) (see the Example provided herein). All the commonly used methods for genome sequence searching rely on similar, statistically derived, scoring matrices. Frequently, the same scoring matrix is used to search for related sequences (for example, with a tool available under the trademark of BLAST), to prepare a multiple alignment of the protein sequences, to analyze sequence conservation, and finally, to locate distant relatives of the family according to motif conservation. The present invention, using PCP motifs, provides an alternative and an independent way to identify distantly related proteins based on sequence information.

For example, when the human APE1 sequence was used as a query for a search using a tool available under the trade designation PSI-BLAST in the ASTRAL40 structural database with default parameters, neither known homologue of this enzyme in the database, bovine DNase-I or synaptojanin, a member of the Inositol 5'-polyphosphate phosphatase (IPP) family, was revealed. A PCP motif search according to the present invention showed, as the highest scoring proteins, all members of the DNase-I like SCOP-superfamily of APE in that database demonstrating that the present invention can find non-trivial relationships between distantly related members within superfamilies. Other high scoring proteins were from different SCOP classifications but shared functions with the APE/DNase-I/IPP superfamily, including phosphatase activity and/or metal ion binding.

Further, the present invention may be used to identify functional areas in related proteins with different overall activities. In other words, besides the demonstrated capability of identifying distantly related proteins (or as a fold recognition tool), detecting PCP signatures or PCP motifs of a protein family is also helpful in identifying critical areas that are important for its function. Such PCP motifs can be further studied instead of the whole protein and these motifs can indicate target areas for developing drugs. Further, at least in one embodiment, by adding a structural definition to the sequence information allows a more focused detection system for determining relatedness of proteins. This use of "molegos," which refers to structurally related sequence motifs, may provide another way to identify functionally important areas of a protein. For example, molegos, and use thereof, are described in Schein, et al., Total sequence decomposition distinguishes functional modules, "molegos" in apurinic/apyrimidinic endonucleases, *BMC Bioinformatics*, 3, 37 (2002), which is entirely incorporated herein.

The present invention uses specific mathematical tools which have been derived to locate PCP motifs in aligned protein sequences and to correlate sequences with structure and function. The present invention relies directly on the physical-chemical properties of amino acids and is substantially faster, relative to other methods, such as those based on neural networks or fold recognition tools. The present invention automatically identifies PCP motifs that can be used to detect common elements in proteins that share no global sequence identity.

Other methods that define motifs based on expert knowledge (e.g., such as those described in Falquet et al., The PROSITE database, its status in 2002, *Nucleic Acids Res*, 2002, 30: 235-238; and Truong et al., Identification and characterization of subfamily-specific signatures in a large protein superfamily by a hidden Markov model approach, *BMC Bioinformatics*, 2002, 3(1): 1) or groups of similar amino acids have just recently been described (e.g., such as in Ben-Hur et al., Remote homology detection: a motif based approach, *Bioinformatics*, 2003, 19(Suppl. 1): i26-i33) but are significantly different from the method according to the present invention.

Databases that have been assembled with expert user knowledge, such as the PROSITE database (available at the website us.expasy.org/prosite/), which is a summary of data that may occur in other databases as well, is a list of motifs that have been defined as specific for a protein family. The syntax of the motif data storage system is limited to those specifically defined by the expert defining the motifs. The motifs are not automatically derived and are described in alphabetic fashion, and not according to physical chemical properties as in the method described according to the present invention.

The motifs defined by the E-motif program (available at the website fold.stanford.edu) are automatically derived but are not defined according to aggregate physical chemical properties in a systematic fashion such as that described according to the present invention. The approach to sequence database searching is different and less systematic than that according to the present invention. Neither the E-motif nor the PROSITE approach seeks to link structural data to further define motifs in the form of molegos, conserved units in protein families that are conserved in both structure and sequence.

Further, for databases, the motifs are defined to discriminate one protein family from another. At least in one embodiment of the present invention, the novelty of the approach according to the present invention is that the PCP motifs are used to completely describe the functions and structural characteristics of a given protein family. As such, motifs (and molegos) can be defined as specific for a protein with a given function, or as general (or generic) to many different types of proteins that may share a common function. Hence, the method may be referred to as "total sequence decomposition" and, at least in one embodiment, is distinguished by the programs according to the present invention being prepared to perform such decomposition automatically so as to be applicable to genomic database screening.

One or more various embodiments of the illustrative sequence data analysis method 30, shown generally in FIG. 2, shall be described with reference to FIGS. 3-8. The provision of the multiple sequence alignment (block 32), shown generally in FIG. 2, may be provided by any suitable alignment tool. For example, such alignment tools include those available under the trademark of BLAST available on the internet through the National Center for Biotechnology Information (NCBI) (website .ncbi.nlm.nih.gov/BLAST), those available under the trade designation of CLUSTALW available on the internet through the European Bioinformatics Institute (EBI) (website ebi.ac.uk/clustalw/), or any other suitable multiple alignment tool.

Figure 3:
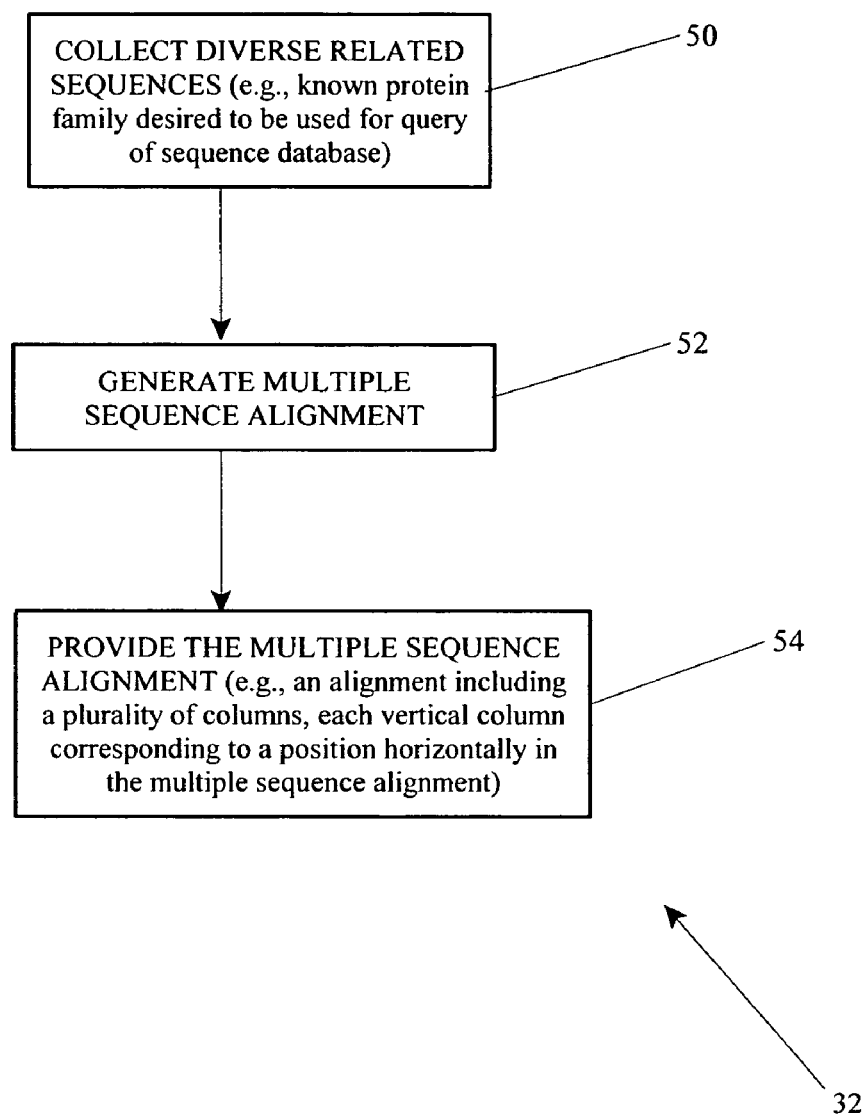
FIG. 3 shows a more detailed block diagram of one illustrative embodiment of a process for providing multiple sequence alignments as generally illustrated in the process of FIG. 2.

One embodiment of providing a multiple sequence alignment 32 is shown in FIG. 3. For example, diversely related sequences may be collected (block 50) by any suitable tool such as that available under the trade designation of BLASTP available on the internet through the National Center for Biotechnology Information (NCBI), or any other suitable tool. In other words, for example, related sequences of a known protein family desired to be used for query of a sequence database may be collected. Thereafter, a multiple sequence alignment is generated (block 52) for the related sequences of the family such as with an alignment tool as described herein. Further, the multiple sequence alignment is provided for use by the PCP motif generation program (block 54).

For example, according to one embodiment of the present invention, the multiple sequence alignment includes a column of aligned amino acids and/or gaps for each of a plurality of horizontal positions of the multiple alignment. In other words, the alignment may include q sequences and be defined using s columns. In such a case, the alignment takes the form of a matrix of amino acid codes and gaps which can be expressed as s×q. A file representative of the multiple sequence alignment may then be provided for use in generating PCP motifs (block 34) of the sequence data analysis method 30.

The PCP motif generation process 34 is further described in detail with reference to FIGS. 4 and 5. As shown in the block diagram of FIG. 4, the PCP motif generation process 34 is provided with the multiple sequence alignment (block 60), such as that provided as described with reference to FIG. 3. Further, multidimensional numerical PCP descriptors for each amino acid based on the physical-chemical properties of each amino acid are provided (block 62) so that the multiple sequence alignment can be quantitatively described in terms of the PCP descriptors as a series of "N" eigenvectors (block 64).

The multidimensional numerical PCP descriptors for each amino acid (block 62) may be determined as described in the article by Venkatarajan and Braun, entitled "New quantitative descriptors of amino acids based on multidimensional scaling of a large number of physical-chemical properties," *J Mol. Model.* (2001) 7: 445-453, which is entirely incorporated herein by reference. As described therein, quantitative descriptors for the 20 naturally occurring amino acids based on multidimensional scaling of 237 physical-chemical properties are provided. In one embodiment, a five-dimensional property space can be constructed such that the amino acids are in a similar spatial distribution to that in the original high-dimensional property space. Properties that correlate well with the five major components were hydrophobicity, size, the relative tendency for each of the amino acids to occur in α-helices, the number of degenerate triplet codons that could encode the amino acid and the frequency of occurrence of amino acid residues in β-strands.

The quantitative descriptors summarize information about physical-chemical properties that are useful in identifying protein homologues on the basis of PCP-based motifs. Multidimensional scaling of some or all of 237 physical-chemical properties can be used to derive quantitative descriptors for all 20 naturally occurring amino acids, and the main variations of all properties for the 20 amino acids can be reduced, for example, through five quantitative descriptors. Multidimensional scaling is a general classification approach to reconstructing the geometrical configuration of large point sets in lower dimensions. While the physical meaning of each descriptor can be correlated with individual properties, the five descriptors cannot simply be replaced by five individual properties.

The quantitative descriptors described in Venkatarajan and Braun (2001), or as otherwise developed using the same or similar techniques, can be used to characterize PCP motifs in protein families through employment of the present invention.

In one particular embodiment of providing the quantitative descriptors, each property was normalized, where S is normalized property values, a is the index of the property and i stands for the amino acid. P is the property value, $\overline{P}_\alpha$ and $\sigma_{P\alpha}$ are the average and the standard deviation of property α.

Each amino acid i is represented as a vector $\underline{S}(i)$ in a 237-dimensional continuous space, where the components $S_\alpha(i)$ are the normalized property values. The scalar product $Q_{ij}$ between two vectors $\underline{S}(i)$ and $\underline{S}(j)$, where j is another index for an amino acid, is given by $$Q_{ij} = S(i) \cdot S(j)$$

$$Q_{ij} = \sum_{\alpha=1}^{237} S_\alpha(i) \cdot S_\alpha(j)$$

The positive symmetric 20×20 matrix Q consists of the scalar products of the property vectors $\underline{S}(i)$ and $\underline{S}(j)$, where i=1 . . . 20 and j=1 . . . 20.

Eigenvectors E and eigenvalues λ of the matrix Q can be computed using the JACOBI and EIGSRT subroutines provided in Numerical Recipes (Press, W. H., Teukolsky, S. A., Vettering, W. T., Flannery, B. P., 1999, "Numerical recipes in C", Cambridge University Press, New York).

$$Q \cdot E = \lambda E$$

As Q is of order 20, there will be 20 eigenvectors and eigenvalues λ and the smallest eigenvalue $\lambda_{20}$ is equal to 0 due to normalization of the properties. The subroutine JACOBI implements a Jacobian transformation of a symmetric matrix and returns the eigenvectors and values of the Q matrix. The eigenvalues and their corresponding eigenvectors can be indexed in decreasing order of the eigenvalues.

If $\mu$ represents the index of eigenvalue and eigenvector, then the elements of the Q matrix can be equated to eigenvalues and eigenvectors as:

$$Q_{ij} = \sum_{\mu=1}^{20} \lambda_\mu E_i^\mu \cdot E_j^\mu$$

The first five significant eigenvalues were selected for the representation of amino acids, thus $Q_{ij}$ can be written as:

$$Q_{ij} \approx \sum_{\mu=1}^{5} \lambda_\mu E_i^\mu \cdot E_j^\mu$$

Each amino acid can be represented as a vector in the five-dimensional Euclidean space (a.k.a. Eigen sub-space) with each dimension perpendicular to each other. The coordinates of the ith amino acid can be written as:

$$\sqrt{\lambda_{\mu=1}}E_i^{\mu=1}, \sqrt{\lambda_{\mu=2}}E_i^{\mu=2}, \sqrt{\lambda_{\mu=3}}E_i^{\mu=3}, \sqrt{\lambda_{\mu=4}}E_i^{\mu=4}, \sqrt{\lambda_{\mu=5}}E_i^{\mu=5}$$

The distance between the ith and jth amino acids is given by:

$$d_{ij} = \sqrt{\sum_{\mu=1}^{5} (\sqrt{\lambda}_\mu E_i^\mu - \sqrt{\lambda}_\mu E_j^\mu)^2}$$

Distances computed between amino acids in the five-dimensional Eigen sub-space constitute the property distance matrix (PDM). Small distance values between two amino acids indicate they are similar in all of their 237 physical-chemical properties.

The distribution of the eigenvalues of the Q matrix, containing the scalar products between all pairs of the 237-dimensional amino acid vectors, rapidly decreases from the largest value $\lambda_1=1962$ to $\lambda_{19}=16$. The rapid decrease of the eigenvalues derived from the 237 physical-chemical properties suggests that the number of properties can be reduced while retaining approximately the same distribution of amino acids in the property space. The eigenvalues rapidly decrease within the five largest eigenvalues. As such, the first five eigenvalues and eigenvectors can be used to calculate five-dimensional numerical descriptors of the amino acids. The five numerical descriptors for each amino acid are given in Table 1.

TABLE 1

Components E1 to E5 of 237 physical-chemical properties for each amino acid

| Eigenvalue ($\lambda$) | Eigenvector[a] | | | | |
|---|---|---|---|---|---|
| | E1 1961.504 | E2 788.200 | E3 539.776 | E4 276.624 | E5 244.106 |
| A | 0.008 | 0.134 | −0.475 | −0.039 | 0.181 |
| R | 0.171 | −0.361 | 0.107 | −0.258 | −0.364 |
| N | 0.255 | 0.038 | 0.117 | 0.118 | −0.055 |
| D | 0.303 | −0.057 | −0.014 | 0.225 | 0.156 |

TABLE 1-continued

Components E1 to E5 of 237 physical-chemical properties for each amino acid

| Eigenvalue ($\lambda$) | Eigenvector[a] | | | | |
|---|---|---|---|---|---|
| | E1 1961.504 | E2 788.200 | E3 539.776 | E4 276.624 | E5 244.106 |
| C | −0.132 | 0.174 | 0.070 | 0.565 | −0.374 |
| Q | 0.149 | −0.184 | −0.030 | 0.035 | −0.112 |
| E | 0.221 | −0.280 | −0.315 | 0.157 | 0.303 |
| G | 0.218 | 0.562 | −0.024 | 0.018 | 0.106 |
| H | 0.023 | −0.177 | 0.041 | 0.280 | −0.021 |
| I | −0.353 | 0.071 | −0.088 | −0.195 | −0.107 |
| L | −0.267 | 0.018 | −0.265 | −0.274 | 0.206 |
| K | 0.243 | −0.339 | −0.044 | −0.325 | −0.027 |
| M | −0.239 | −0.141 | −0.155 | 0.321 | 0.077 |
| F | −0.329 | −0.023 | 0.072 | −0.002 | 0.208 |
| P | 0.173 | 0.286 | 0.407 | −0.215 | 0.384 |
| S | 0.199 | 0.238 | −0.015 | −0.068 | −0.196 |
| T | 0.068 | 0.147 | −0.015 | −0.132 | −0.274 |
| W | −0.296 | −0.186 | 0.389 | 0.083 | 0.297 |
| Y | −0.141 | −0.057 | 0.425 | −0.096 | −0.091 |
| V | −0.274 | 0.136 | −0.187 | −0.196 | −0.299 |

[a] The numerical descriptors for each amino acid i are calculated by $\sqrt{\lambda_\mu}E_i^\mu$ for the five eigenvectors $E^\mu$, $\mu = 1 \ldots 5$.

Further, the quantitative descriptors represent a precise spatial relation of all amino acids with respect to many physical-chemical properties.

Although the above embodiment describes the use of five-dimensional descriptors, it will be recognized that any number of N-dimensional descriptors may be used. In other words, the quantitative descriptors may be based on more or less than five eigenvectors for the amino acids. However, in one preferred embodiment, five-dimensional quantitative descriptors for the physical-chemical properties for each amino acid are provided. In other words, the numerical PCP descriptors for each amino acid include a numerical descriptor for each of a plurality of N eigenvectors (e.g., five eigenvectors where five-dimensional descriptors are used).

Figure 4:
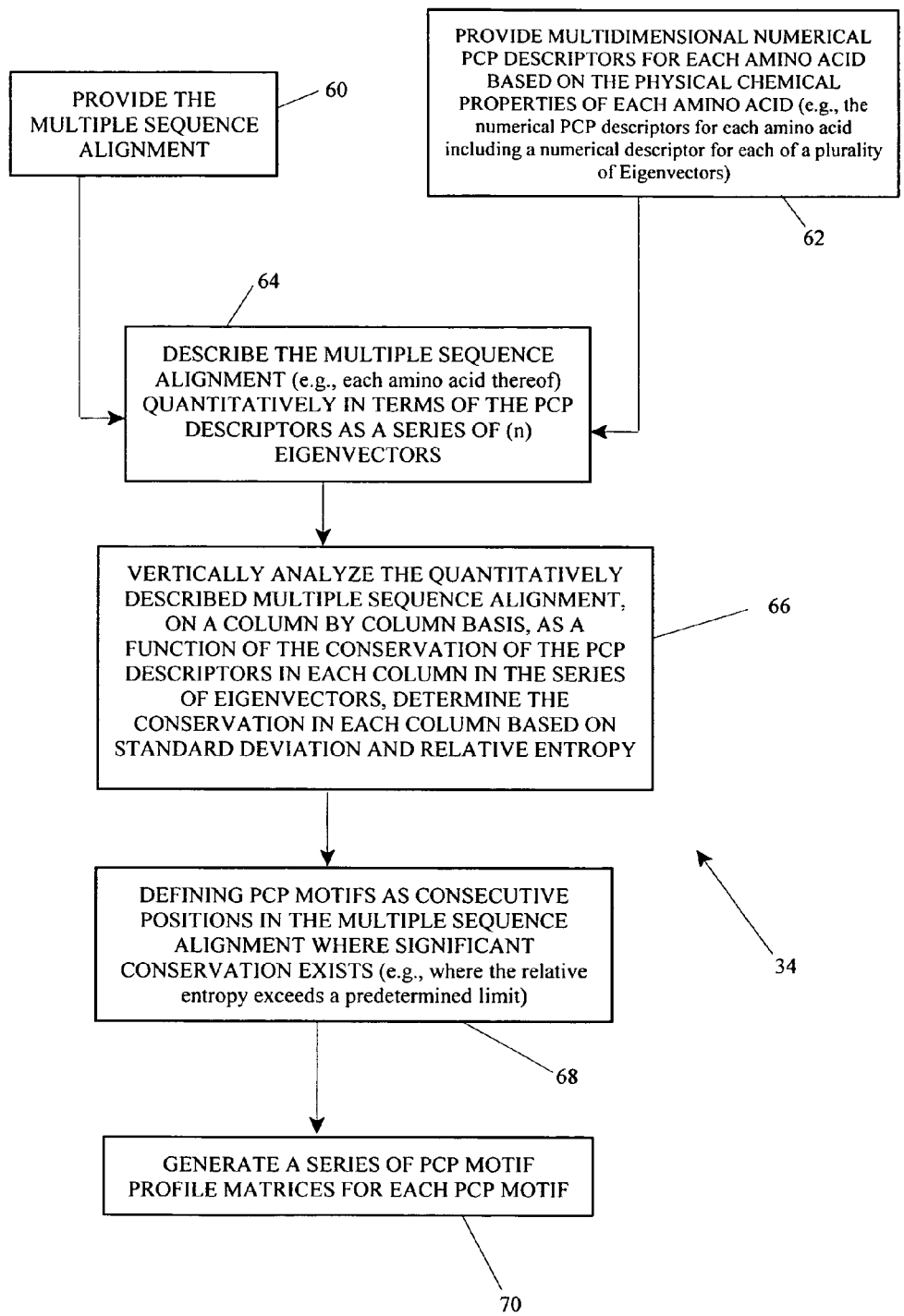
FIG. 4 shows a more detailed block diagram of one illustrative embodiment of a process for generating physical-chemical property motifs as shown generally in the process of FIG. 2.

Further, with reference to FIG. 4, after the multiple sequence alignment is quantitatively described in terms of the PCP descriptors as a series of N eigenvectors (block 64), the quantitatively PCP described multiple sequence alignment is analyzed based on the conservation of the PCP properties at each horizontal position of the alignment (block 66). As shown generally by block 66, the quantitatively PCP described sequence alignment is analyzed, on a column-by-column basis (i.e., for each horizontal position of the alignment), as a function of the conservation of the PCP descriptors in each column in the series of eigenvectors. The conservation is measured using standard deviation of the values of the PCP descriptors for each column analyzed and the related relative entropy for the analyzed column.

Generally, PCP motifs may be defined for the multiple sequence alignment at consecutive positions of the multiple sequence alignment where significant conservation exists, for example, where the relative entropy exceeds a predetermined limit at consecutive horizontal positions of quantitatively PCP described alignment (block 68). Once the PCP motifs have been defined, a series of PCP motif profile matrices may be generated for each PCP motif (e.g., a multi-dimensional matrix) (block 70), such as for use in data mining of a sequence database (block 36, FIG. 2).

In other words, when considering a five-dimensional space configuration, the quantitative descriptors $E^1$ to $E^5$ for amino acid properties and their physical interpretation are deduced from a comprehensive list of 237 physical-chemical properties; the five components $E^1$ to $E^5$ will in general be differently conserved in each column (k) of the aligned sequences of a protein family. The conservation within a column of the multiple alignment can be measured by standard deviations $\sigma_k^i$ of the numerical values at that position for eigenvectors $E^1$ to $E^5$ (where i varies from 1-5) and by the relative entropy $\Re_k^i$, also referred to as Kullback-Leibler distance (Kullback, S. and Leibler, R. A., 1951, "On information sufficiency", *Annals Math. Slat.*, 22, 79-86), that describes the relative conservation of the amino acids in the column as compared to that expected for a random distribution. The component index i varies from 1 to 5, where n=5-dimensional space is used. The quantities $\sigma_k^i$ and $\Re_k^i$ are calculated across the residues in each column k in the PCP descriptor described alignment of the protein family of sequences (block 66).

Five equally spaced bins characterize the distributions of the E1 to E5 values for each of the components. The difference between the observed distribution for the component $E^i$ at column k and the background distribution can be calculated by the relative entropy $\Re_k^i$:

$$\Re_k^i = \sum_{b=1}^{5} Q(X^b) \log_2\left(\frac{Q(X^b)}{P(X^b)}\right)$$

$Q(X^b)$ is the observed fraction of the component i in the bin b and $P(X^b)$ is the corresponding background frequency. For significantly conserved properties, the distributions of the component values $E^1$ to $E^5$ are narrower than the background distributions derived from the 'a priori' occurrences of amino acids; i.e., low standard deviations and high relative entropy values would be characteristics of such significantly conserved properties. If the distributions of the observed frequencies of the components are equal to that of the background frequencies, then $\Re$ will be zero, otherwise it will be positive. High relative entropy values indicate a significant difference between the observed frequencies of distributions in a column and the 'a priori' background distribution.

PCP motifs may be defined as contiguous horizontal positions in a multiple alignment where residues are significantly conserved according to one of the principal components $E^i$, that is those columns k where the relative entropy $\Re_k^i$ of at least one component $E^i$ is above a $\Re$-cutoff value (block 68). A minimum length cutoff (L-cutoff) is provided by the user to define PCP motifs of sufficient length. The user can also specify a G-cutoff parameter (i.e., a gap limit) to define the maximum number of insignificant positions between two significant positions in a PCP motif. Default values of the parameters $\Re$-cutoff, L-cutoff and G-cutoff can be determined empirically.

Each PCP motif identified in the PCP described alignment may be quantitatively expressed as a profile including the average values, standard deviations, and the relative entropies for each eigenvector E1-E5 at each horizontal position of the alignment (i.e., corresponding to each column in the alignment). Such values are used to generate a PCP motif profile matrix (block 70) for use in data mining of a sequence database.

Figure 5:
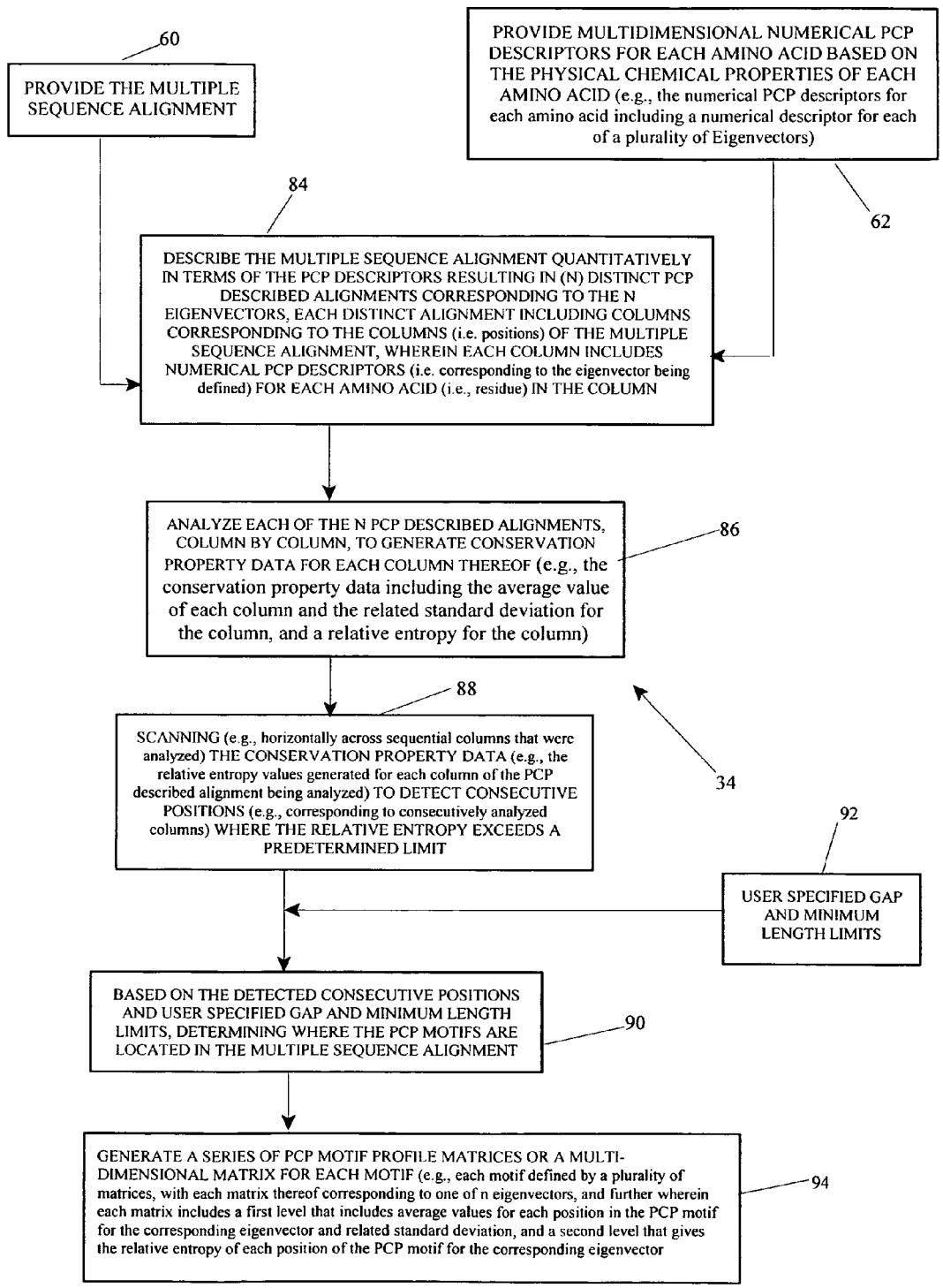
FIG. 5 shows yet another block diagram of one illustrative embodiment of a process for generating physical-chemical property motifs as generally shown in the process of FIG. 2, and also shown in the more detailed process of FIG. 4.

FIG. 5 provides a more detailed block diagram of the PCP motif generation process 34 according to one embodiment of the present invention. As shown therein, with provision of the multiple sequence alignment (block 60) and the provision of multidimensional numerical PCP descriptors (block 62), each amino acid of the multiple sequence alignment can be quantitatively described in terms of the PCP descriptors resulting in a plurality of distinct PCP described alignments (block 84). Each distinct PCP described alignment corresponds to and is defined with numerical PCP descriptors that correspond to one of the N eigenvectors. Further, each distinct PCP described alignment includes a plurality of columns of descriptor values (e.g., values that correspond to the appropriate eigenvector) corresponding to the columns in the multiple sequence alignment.

For example, the plurality of distinct PCP described alignments that represent the multiple sequence alignment can be considered to include N distinct s×q matrices, where s is the number of horizontal positions or columns of the alignment and q is the number of sequences. Each PCP described alignment or matrix includes descriptor values for the amino acids corresponding to the respective eigenvector of the series of eigenvectors to which the alignment corresponds (e.g., the gaps being left as zero). For example, a PCP described alignment corresponding to eigenvector E1 would include amino acid numerical descriptors corresponding to the eigenvector E1, a PCP described alignment corresponding to eigenvector E2 would include amino acid numerical descriptors defined for the E2 eigenvector, and so forth. In other words, the multiple sequence alignment is described quantitatively in terms of PCP descriptors for eigenvectors E1-E5 for a five-dimensional configuration. Such a series of PCP described alignments may be thought of as a multi-dimensional alignment with the third dimension being N, where N is the number of eigenvectors or dimensional space being used (e.g., 5-dimensional space); the other dimensions including s and q.

Each distinct PCP described alignment (e.g., corresponding to E1-E5 and including five alignment matrices in a five-dimensional configuration) is analyzed (block 86). Such analysis is done on a column-by-column basis for each horizontal position of each PCP described alignment to generate conservation property data corresponding thereto. In other words, each column of a PCP described alignment is analyzed. Such analysis results in values to be used in detecting conservation of the PCP characteristics. The values for each column include an average value of the PCP descriptors of each column and the associated standard deviation along the column being analyzed, as well as a relative entropy for the column being analyzed (see description provided with reference to FIG. 4 for algorithms to provide such values). Such values are determined for each horizontal position (i.e., s) in the PCP described alignment. Further, each PCP described alignment (e.g., five alignments in the 5-dimensional configuration) is likewise analyzed.

Thereafter, the conservation property data generated for each of the PCP described alignments (i.e., corresponding to each of the eigenvectors being considered) is scanned (e.g., the conservation property data generated for each column or horizontal position of the alignment is scanned) to detect consecutive horizontal positions of the alignment (i.e., columns of an alignment) where the relative entropy exceeds a predetermined limit (block 88). The predetermined limit is set by a user and determined as a function of the sequence variability of the protein family under consideration.

Based on the detected consecutive positions (block 88) and also user-specified gap and minimum length limits (block 92), PCP motifs are located in the multiple sequence alignment (block 90). The user-specified gap and minimum length limits (block 92) are user input values. In other words, as a result of the detected consecutive conserved positions and user-specified gap and minimum length limits, PCP motifs in the original multiple sequence alignment are defined. It is noted that such conservation may be detected with respect to any of the eigenvectors (e.g., represented by the respective PCP described alignments) resulting in a PCP motif related to such detected conservation. A list of the PCP motifs may then be provided in a desired form (e.g., a listing of the columns of the multiple sequence alignment identified). The list of such PCP motifs may be printed out or saved to a file.

The program may then generate a series of PCP motif profile matrices for each PCP motif (block 94). Each matrix of the series of PCP motif profile matrices corresponds to one of N eigenvectors. The program compiles values for each horizontal position (e.g., column) of the PCP motif to be used in a corresponding profile matrix. The values for each PCP motif profile matrix include the average value of the PCP descriptors for each horizontal position in the PCP motif (e.g., those amino acid descriptors, for the corresponding eigenvector, provided for each residue in each column of the PCP motif), and the standard deviation associated with the average value, as well as the relative entropy for the horizontal position in the motif (e.g., column of the PCP motif).

As such, at least in one embodiment, the series of PCP motif profile matrices could be expressed as a multi-dimensional matrix, m×n(p), where n is the number of eigenvectors and m is the number of horizontal positions (e.g., columns) in the PCP motif, and further wherein p are the number of values generated for the matrix (e.g., where p is 3 when the values include average value, standard deviation and relative entropy).

Further, in another embodiment, each of the series of PCP motif profile matrices may each include a first level that includes an average value of PCP descriptors for each horizontal position in the PCP motif for the corresponding eigenvector and the standard deviation associated therewith, and a second level that gives the relative entropy for each horizontal position (i.e., column) of the PCP motif for the corresponding eigenvector.

With further reference to FIG. 2, after generation of the PCP motifs (block 34), such PCP motifs may be used for mining sequence data to locate related segments of protein sequences in a database having PCP characteristics similar to the PCP motifs (block 36). The series of PCP motif profile matrices (or multidimensional matrix) for each PCP motif can be used to perform such data mining.

Figure 6:
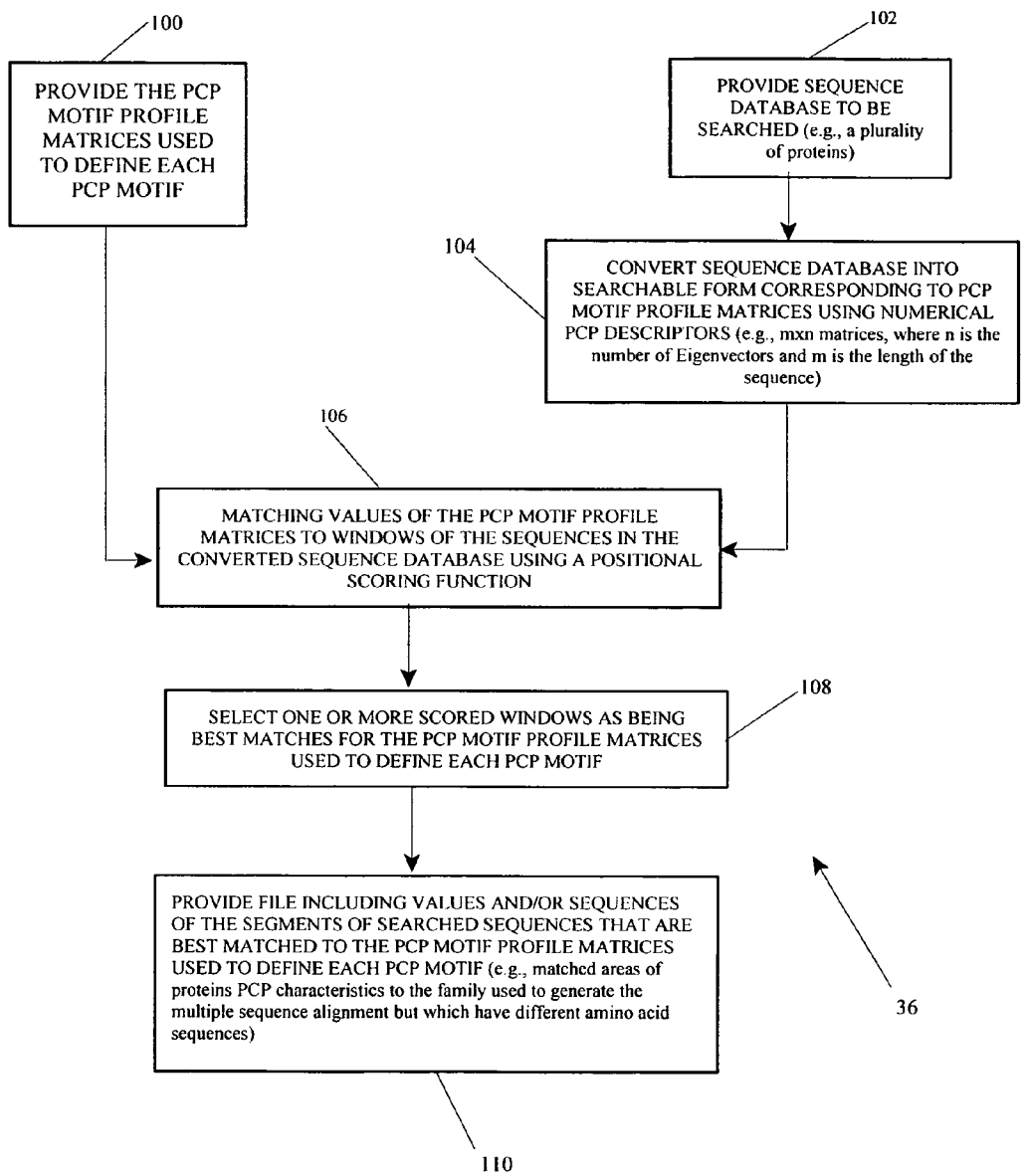
FIG. 6 shows a more detailed block diagram of one illustrative embodiment of a data mining process as generally illustrated in the process of FIG. 2.

FIG. 6 provides one embodiment of a data mining process 36 that may be used according to the present invention. One will recognize that although a positional scoring function is utilized in this particular embodiment, that one or more other types of scoring functions, including other positional scoring functions, may be utilized to match PCP motif profile matrices to segments of sequence data being searched. Generally, any scoring function that relates the sequence windows of the database in a probabilistic fashion to the average values of the properties determined for the motifs (block 94) can be used. However, meaningful values can only be obtained if the absolute values are expressed as an expectation value according to the average, or random, distribution of amino acids.

As shown in the block diagram of FIG. 6, in one embodiment of the data mining process 36, the process includes providing one or more PCP motif profile matrices (block 100) and also providing a sequence database to be searched (block 102). The process then uses the values of the PCP motif profile matrices to search, in an automatic fashion, for related segments of protein sequences in the sequence database.

In this embodiment of the data mining process 36, the process provides for conversion of the protein sequences of the database to a searchable form suitable for use with PCP motif profile matrices (block 104). For example, whole sequences are converted to matrices using the numerical PCP descriptors (e.g., m×n matrices, where n is the number of eigenvectors and m is the length of the sequence). Further, for example, nucleotides (e.g., RNA, DNA) may be converted to amino acid sequences, and thereafter to a suitable and searchable form. The term sequence database includes the searching of nucleotides as well as amino acid lists).

Values of the PCP motif profile matrices are then matched to the converted sequence matrices using a positional scoring function (block 106). In one embodiment, for example, a Lorentzian based scoring scheme may be used to measure the quality of fit for a database sequence to a PCP motif profile matrix at position k for the component eigenvector i. The PCP motif profile matrix at a significant position k (defined by the relative-entropy cutoff) includes an average of component magnitudes $<E_k^i>$ and the standard deviation $\sigma_k^i$. If $E^i$ is the magnitude of PCP component i observed in the query sequence, the Z value is calculated:

$$Z_k^i = \left(\frac{E^i - \langle E_k^i \rangle}{W\sigma_k^i + \Phi}\right)$$

$$S_k^i = \left(\frac{1}{1 + Z_k^i * Z_k^i}\right)$$

Where W is the weight for standard deviation (e.g., set to 1.5 in one embodiment to perform calculations) and $\Phi$ is a small positive shift (e.g., set to 0.001 in one embodiment) added to the denominator to prevent overflow during calculation when $\sigma_k^i$ is zero. The individual score for each component is then added for significantly conserved property components along the length of the motifs to obtain a window score $S_w$ and a maximum possible score $S_{max}$ calculated by adding 1 for every significant position:

$$S_w = \sum_{i,k} S_k^i$$

$$S_{max} = \sum_{i,k} 1$$

The final fractional score for the window is:

$$S_{wfraction} = \frac{S_w}{S_{max}}$$

Thereafter, at least in one embodiment, the process 36 selects, for each protein in the sequence database, the highest scoring window as being the best segment match for the series of PCP motif profile matrices defining the PCP motif (block 108) for that particular protein. For example, the program may select, for each protein in sequence database being searched, the highest scoring window, and store it in a file or temporary buffer (e.g., a data file that may be used by one or more subsequent programs or processes). One will recognize that multiple high scoring segments may also be selected, and the present invention is not limited to just the highest scoring window.

As shown in block 110, a file is provided including values and/or sequences of the segments that are best matched to the PCP motif profile matrices. In other words, the file may include values and sequences of highest scoring segments for each protein in the searched database. Such matched areas of the proteins have similar physical-chemical properties to the average value for the sequence family used to generate the multiple sequence alignment but may include a different amino acid string than a consensus sequence generated from the multiple sequence alignment according to a conventional method.

For conditions or applications where a user only desires to find which areas of a protein are best matched to the list of PCP motifs, the program may provide the file and no other processing need be performed. However, optionally, such located segments that match the PCP motifs can further be used to rank the proteins of the database according to their similarity to the original family of protein sequences used to generate the multiple sequence alignment. For example, the data mined from the exemplary embodiment of FIG. 6 may be provided for use in determining which proteins of the sequence database most resemble the original family of proteins used to provide the multiple sequence alignment (block 40). Several related protein ranking processes (e.g., selection processes) are described further herein with reference to FIGS. 7 and 8.

Figure 7:
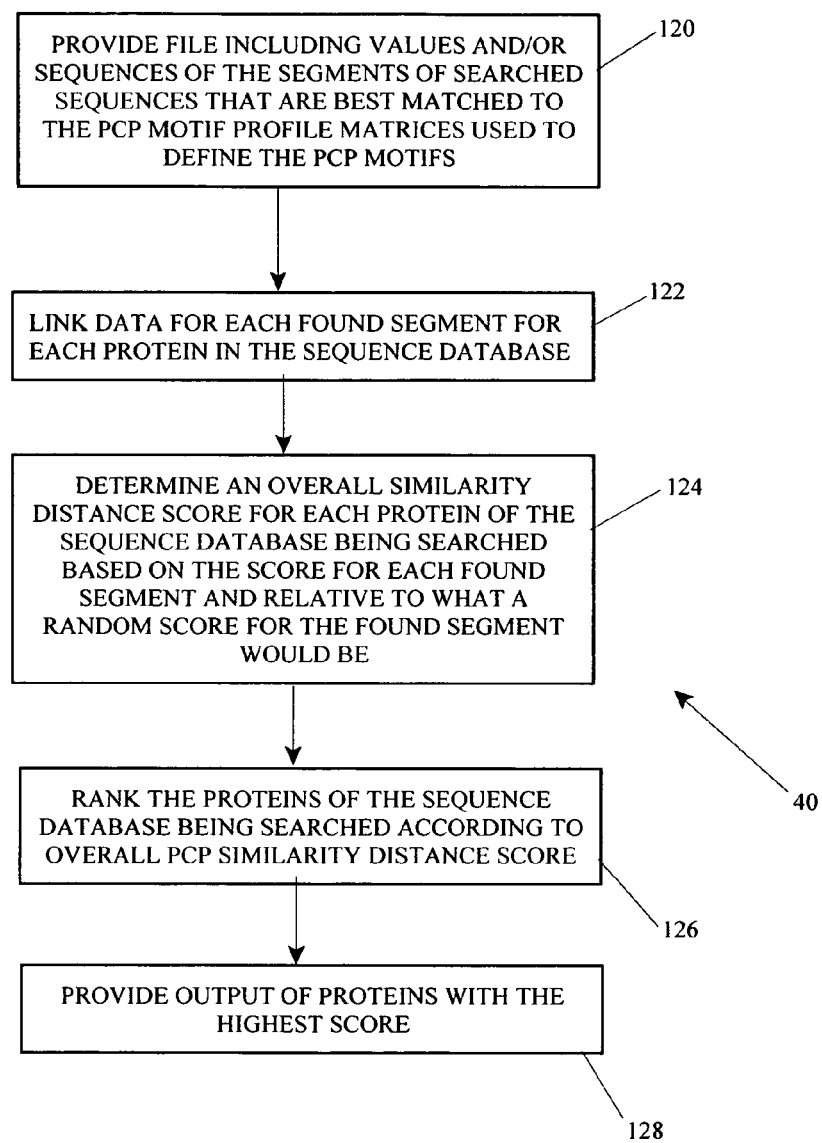
FIG. 7 shows a more detailed block diagram of an illustrative embodiment of a protein ranking process shown generally in the process of FIG. 2.

As shown in the block diagram of FIG. 7, one embodiment of the related protein ranking process 40 includes providing the output of the positional scoring function process, including the scoring data for the highest scoring segments as described with reference to FIG. 6 (block 120). In other words, for each of the proteins in the sequence database, the highest scoring window (or windows) for each of the PCP motifs is selected.

In one embodiment, an optional linking process is performed to link the data for each protein. For example, in one embodiment, the PCP motifs are individually matched, in consecutive order, and a final list of each highest scoring window in each sequence in the database is stored. The lists are then linked for each protein after mining process is performed (block 122). As an alternative, each sequence may be individually evaluated and summarized, which may save storage for large sequence databases.

Thereafter, an overall similarity distance score for each protein of the sequence database being searched is calculated or otherwise determined, based on the score for each of the highest scoring segment of each protein and relative to what a random score would be for the segment (block 124).

In one embodiment, a Bayesian scoring function is used to determine the overall similarity distance for scoring the proteins. For example, a Bayesian method is used to decide if a given score S for a segment in an arbitrary searchable sequence is a sufficient match to a PCP motif, relative to what a random sequence would score. The conditional probability $P(X \in PCP|S)$ that the queried sequence X contains a PCP motif for a given score S is given by Bayes theorem:

$$P(X \in PCP|S) = \frac{P(S|X \in PCP) \cdot P(PCP)}{P(S)}$$

$P(S|X \in PCP)$ is the probability of finding a motif with score S in the sequence family used to generate the PCP motif. $P(S)$ is the probability of finding a PCP motif with similar score in all proteins in the database being searched, and $P(PCP)$ is the probability of finding sequences of the family in the searched database. The empirical distributions of scores in the sequence family and searched database are approximated as a Gaussian distribution:

$$P(S|X \in PCP) = \frac{1}{\sigma\sqrt{2\pi}} e^{\frac{-1}{2\sigma^2}(S-\overline{S}_{PCP})^2}$$

Here, $\overline{S}_{PCP}$ is the average score for the PCP motif and $\sigma$ is the corresponding standard deviation. The probability of finding a PCP motif with similar score in the searched database (DB) is:

$$P(S) = \frac{1}{\sigma\sqrt{2\pi}} e^{\frac{-1}{2\sigma^2}(S-\overline{S}_{DB})^2}$$

Substituting the above two expressions into Bayes theorem, and simplifying by assuming that the standard deviation of scores for PCP and the searched database are similar, we obtain:

$$P(X \in PCP|S) = e^{\frac{\Delta\overline{S} \cdot (S-\overline{S})}{\sigma^2}} \cdot P(PCP)$$

Here, $\overline{S}$ is the average and $\Delta\overline{S}$ is the difference between average scores of a PCP motif in the searched database. The conditional probability that a PCP motif m was found in a searchable sequence X with a score less than or equal to an observed score $S_m$ is given by:

$$P(X \in PCP|S \le S_m) = P(PCP) \cdot \int_0^{S_m} e^{\frac{\Delta\overline{S}_m (S-\overline{S}_m)}{\sigma_m^2}} dS$$

$$P(X \in PCP|S \le S_m) = P(PCP) \cdot \left[\frac{\sigma_m^2}{\Delta\overline{S}_m} e^{\frac{-\Delta\overline{S}_m \overline{S}_m}{\sigma_m^2}}\right] \cdot \left[e^{\frac{\Delta\overline{S}_m S_m}{\sigma_m^2}} - 1\right]$$

We compute a total sequence score $S_x$ over all NP PCP motifs located in the family of sequences (e.g., the multiple sequence alignment) as:

$$S_X = \sum_{m=1}^{NP} \log_2[P(X \in PCP|S \le S_m)]$$

$$S_X = \sum_{m=1}^{NP} \log_2\left[\frac{\sigma_m^2}{\Delta\overline{S}_m} e^{\frac{-\Delta\overline{S}_m \overline{S}_m}{\sigma_m^2}}\right] +$$

$$\sum_{m=1}^{NP} \log_2\left[e^{\frac{\Delta\overline{S}_m \cdot S_m}{\sigma_m^2}} - 1\right] + NP * \log_2 P(PCP)$$

The first and the third terms of the last equation are constant for a given database so the middle term is used for a final scoring and ranking of proteins.

As a result of the Bayesian scoring method, an overall PCP similarity score is provided for the proteins of the sequence data being searched and such scores may be ranked (block 126). With use of the ranked proteins in the searched database, according to their similarity distance score, an output file, including the proteins with the highest score(s) (block 128), can be provided to a user as requested. For example, a user may desire receipt of the top four highest scoring proteins to be listed at the user interface.

Figure 8:
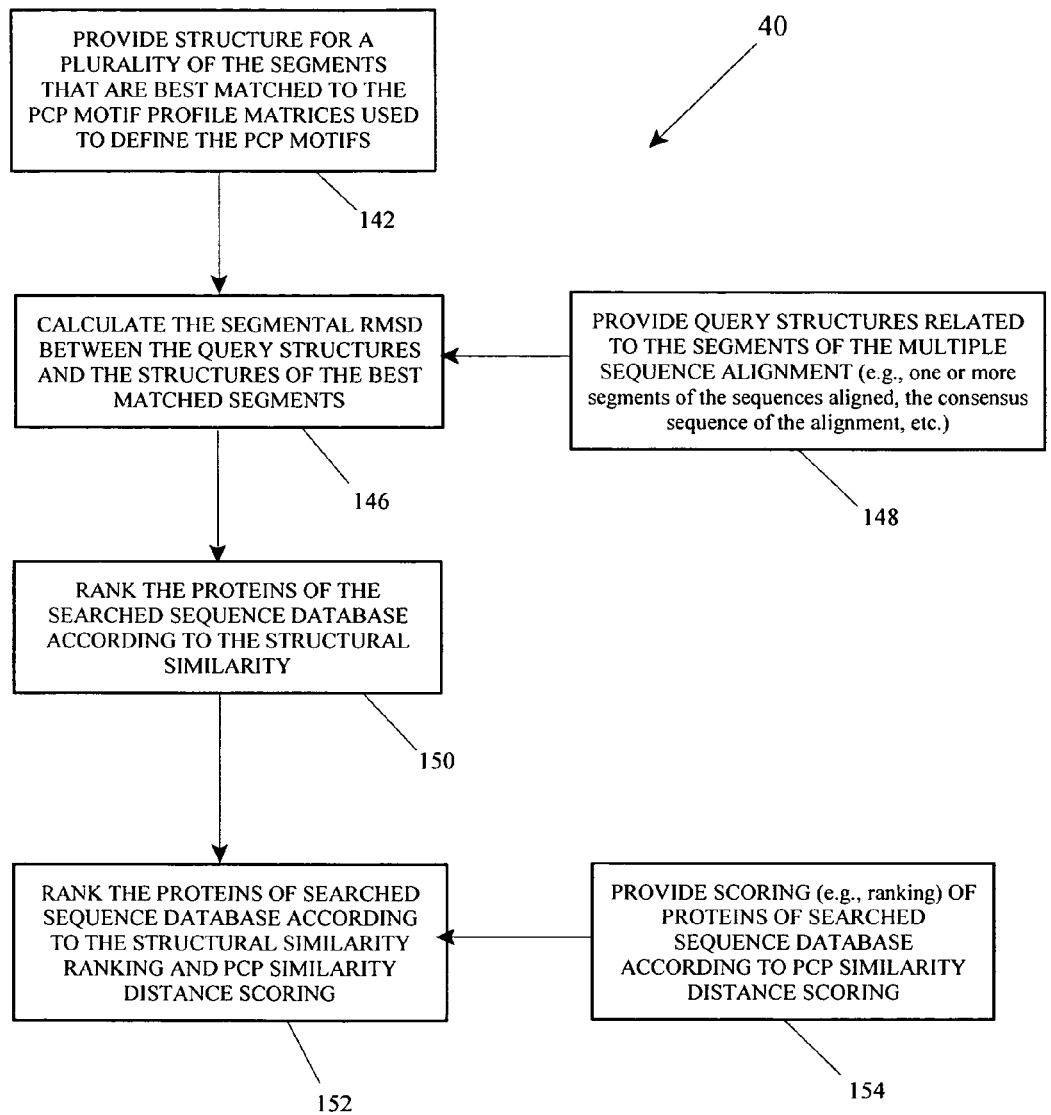
FIG. 8 shows yet another block diagram of another protein ranking process as shown generally in the process of FIG. 2.
Figure 12A:
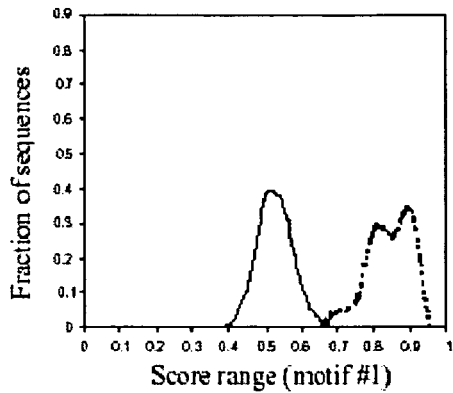
FIGS. 12A-12L show illustrations of the distribution of the highest scoring window for each motif (from the list of PCP motifs for the APEI family shown in FIG. 9A) in a specific (dotted lines) list of the scores for the 42 APE sequences and in the 3635 sequences of the non-specific ASTRAL40 database (solid lines) for use in describing one example of the use of an analysis process according to the present invention.
Figure 12B:
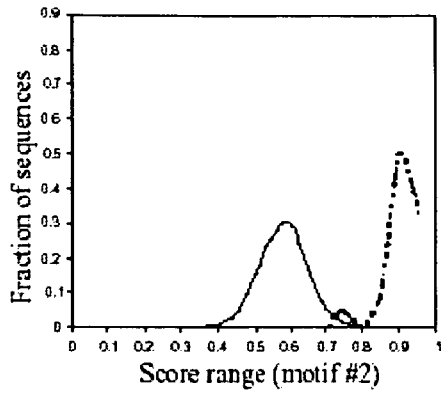
Figure 12C:
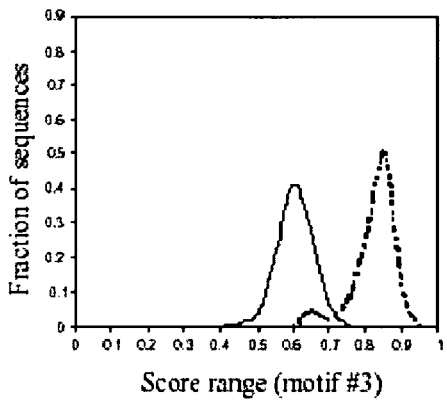
Figure 12D:
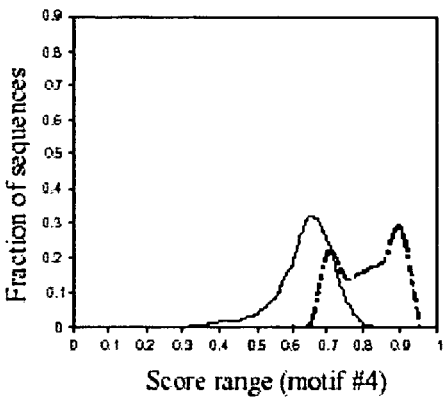
Figure 12E:
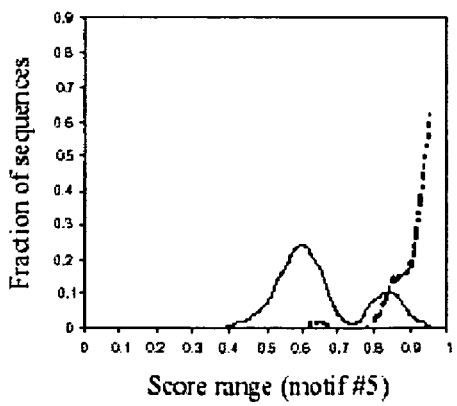
Figure 12F:
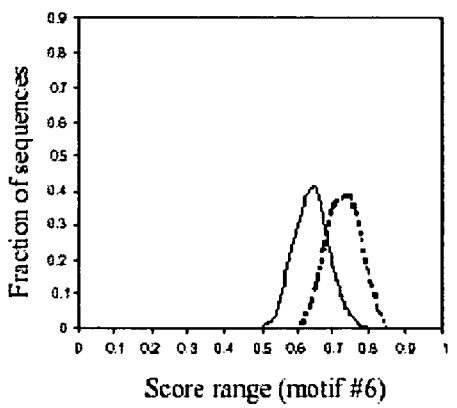
Figure 12G:
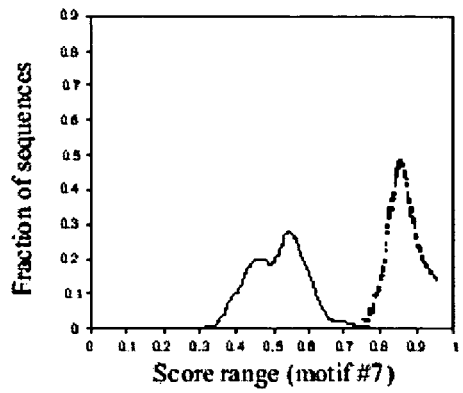
Figure 12H:
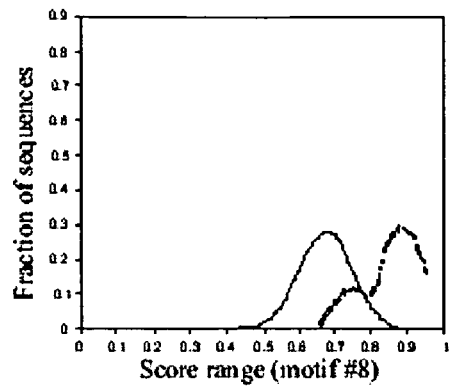
Figure 12I:
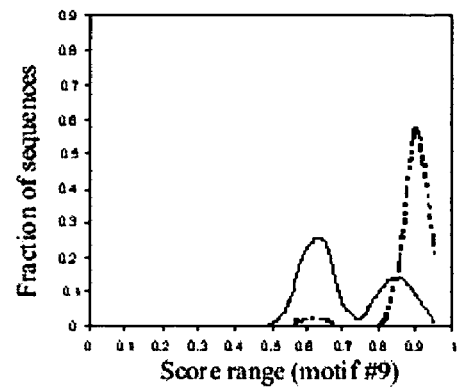
Figure 12J:
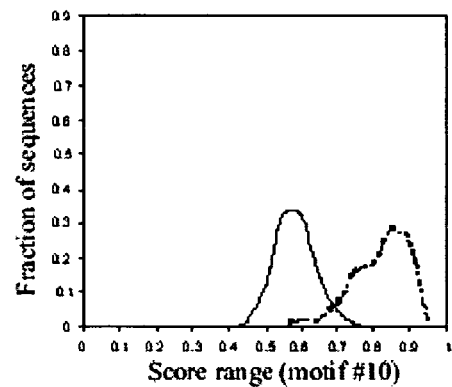
Figure 12K:
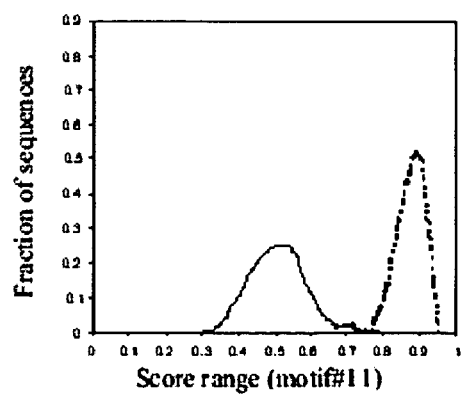
Figure 12L:
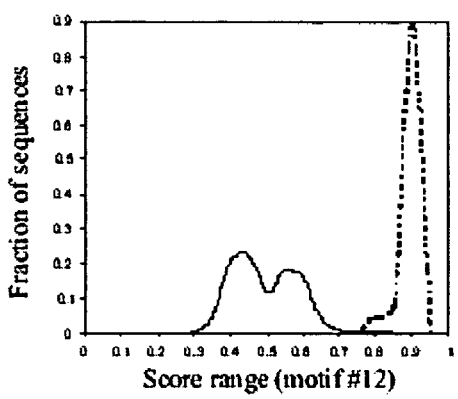

As shown in the block diagram of FIG. 8, structural similarity may be used in combination with PCP similarity (such as described with reference to FIG. 7), or alone, to determine which proteins of the searched sequence data most resemble the multiple sequence alignment. As shown in FIG. 8, the protein ranking process 40, according to yet another embodiment, includes providing a file including structure for a plurality of segments that are best matched to the one or more PCP motif profile matrices (block 142). In addition, query structures related to the PCP motifs of the multiple sequence alignment are also provided (block 148), e.g., molegos. For example, 3D structure relating to one or more proteins of the family of proteins used in providing the original multiple sequence alignment is provided for comparison to the best-matched segments.

The segmental root-mean-square deviations (RMSD) between the query structures and the structures of the best matched segments are calculated (block 146). In other words, at least in one embodiment, after one or more processes detect significant homologues in the sequence database according to purely PCP similarity (e.g., high scoring matches between the PCP motif and segments of proteins in the sequence database), and when 3D structures are available, such calculations may be made. The structure of a relevant comparison protein may be determined experimentally or by theoretical modeling.

As shown in block 150, the proteins of the searched sequence database for which the structural similarity is being compared may be ranked according to structural similarity as determined using the segmental RMSD. Further, scoring of the proteins of the database according to PCP similarity (block 154) may be provided such that the proteins of the searched sequence data may be ranked according to both structural similarity and PCP similarity (block 152) to set forth proteins which most resemble the original family of proteins used to provide the multiple sequence alignment.

EXAMPLE

Use of Present Invention to Determine Distant Homologues of APE1

The following provides one example of the use of a tool according to the present invention. The PCP software tool was used to generate PCP motifs from an alignment of proteins belonging to the DNA repair protein family APE and then search for proteins in the ASTRAL40 database containing similar sequences. The highest scoring proteins were in the DNase-I like SCOP-superfamily of APE, demonstrating that the process according to the present invention can find non-trivial relationships between distantly related members within superfamilies. Other high scoring proteins were from different SCOP classifications (Lo Conte, et al., 2002, SCOP database in 2002: refinements accommodate structural genomics, *Nucleic Acids Res.*, 30, 264-267), but shared functions with the APE/DNase-I/IPP superfamily, including phosphatase activity and/or metal ion binding. Details of the structural and functional roles of the PCP motifs of the APE family are described in Schein, et al., 2002, Total sequence decomposition distinguishes functional modules, "melogos" in apurinic/apyrimidinic endonucleases, *BMC Bioinformatics*, 3, 37.

PCP motifs were generated for the APE protein family. Homologues of human APE1 with E-values less than 0.001 were identified in the NCBI protein sequence database using a search engine available under the trade designation of BLASTP (Altschul, et al., 1997, Gapped BLAST and PSI-BLAST: a new generation of protein database search programs, *Nucleic Acids Res.*, 25, 3389-3402). Sequences from 42 organisms ranging from prokaryotes to eukaryotes were selected (see FIG. 14) after discarding hypothetical APE-like proteins. The taxonomic classification was used to avoid excessive redundancy. Sequences were aligned with a tool available under the trade designation CLUSTALW release 1.8 (Higgins, et al., 2000, Multiple sequence alignment, *Methods Mol. Biol.*, 143, 1-18) using the GONNET similarity matrix (Benner, et al., 1994, Amino acid substitution during functionally constrained divergent evolution of protein sequences, *Protein Eng.*, 7, 1323-1332), with an opening gap penalty of 10.0 and gap extension penalty of 0.2. The sequence alignment was used as input for the PCP generation program for motif identification, as shown and described with reference to FIG. 5.

Each motif identified is quantitatively expressed as a profile, including the average values, standard deviations and the relative entropies for each vector E1-E5 at each position (column in the initial alignment) in the motif. This profile was used to search for similar motifs in the ASTRAL40 sequence database (Brenner, et al., 2000, The ASTRAL compendium for protein sequence and structure analysis, *Nucleic Acids Res.*, 28, 254-256; Chandonia, et al., 2002, ASTRAL compendium enhancements, *Nucleic Acids Res.*, 30, 260-263), which consists of representative sequences corresponding to the SEQRES record of PDB files and classified in SCOP (Lo Conte, et al., 2002, SCOP database in 2002: refinements accommodate structural genomics, *Nucleic Acids Res.*, 30, 264-267). The pairwise identity among the 3635 sequences is less than 40%.

A Lorentzian based scoring system and the Bayesian scoring method described herein were utilized to provide a ranking of the protein sequences in the ASTRAL40 database.

The sensitivity of the present invention to find proteins related to the APEs in the ASTRAL40 database were compared with that of two versions of PSI-BLAST (a trade designation for the tool used) with default parameters (E-value of 0.005), one locally installed (v 2.2.1) and the other on the web at NCBI (Altschul, et al., 1997, Gapped BLAST and PSI-BLAST: a new generation of protein database search programs, *Nucleic Acids Res.*, 25, 3389-3402; Schaffer, et al., 2001, Improving the accuracy of PSI-BLAST protein database searches with composition-based statistics and other refinements, *Nucleic Acids Res.*, 29, 2994-3005). To enhance the ability of a tool available under the trade designation of PSIBLAST to build a profile, the 42 sequences from the APE family, used in the construction of the motifs, were added to the 3635 sequences from the ASTRAL40 database. The human APE sequence was used as query and ran up to five iterations using a tool available under the trade designation of PSI-BLAST. A search for APE related sequences in the BLOCKS database with the default search engine (Henikoff, et al., 2000, Increased coverage of protein families with the Blocks Database servers, *Nucleic Acids Res.*, 28, 228-230; Henikoff, et al., 1999, Blocks+: a non-redundant database of protein alignment blocks derived from multiple compilations, *Bioinformatics*, 15, 471-479; Henikoff, et al., 1994, Protein family classification based on searching a database of blocks, *Genomics*, 19, 97-107) was also performed.

The 'a Priori' Distribution of the Property Components $E^1$ to $E^5$

A comparison was performed for the distribution of the 20 amino acids according to each of the five property components based on an 'a priori' distribution derived from their relative occurrence in the SWISS-PROT (Bairoch, et al., 2000, The SWISS-PROT protein sequence database and its supplement TrEMBL in 2000, *Nucleic Acids Res.*, 28, 45-48) database. The distributions for the five vector components were not uniform, as illustrated for $E^1$ to $E^4$ in FIGS. 10-E1 to 10-E2. For example, the distribution for the component $E^1$, which correlates well with most hydrophobicity scales (Venkatarajan, et al., 2001, New quantitative descriptors of amino acids based on multidimensional scaling of a large number of physical-chemical properties, *J. Mol. Model.*, 7, 445-453), has the most populated bins at the extreme positive and negative values. If the $E^1$ values in a given column of a multiple alignment are concentrated in a narrow range, especially towards the middle range, the distribution of $E^1$ values would differ from the 'a priori' distribution and a high relative entropy value is calculated. A physical interpretation is that the residue hydrophobicity is constrained at that position of the protein family during evolution.

In contrast, the component values for $E^2$, which correlates best with the size/molecular weight of the residues side chains, has a different distribution, with most residues concentrated in the third bin ($5.2 \geq E^2 > 0.2$), and for the fourth vector, which correlates with the natural frequency of occurrence of amino acids (codon degeneracy), bin occupancy decreases as the value of the component $E^4$ increases. A more detailed discussion on the physical interpretation and importance of the vector components $E^1$-$E^5$ is available elsewhere (Venkatarajan, et al., 2001,).

Motifs in the APE Family

The APE1 protein family consists of apurinic/apyrimidinic endonucleases and exonucleases. The MOTIFMAKER subroutine of the "PCPMer" program according to the present invention as described with reference to FIG. 5 identified 12 motifs of various lengths with the cutoff values for entropy, $\Re = 1.25$, for insignificant positions within a motif, G=2, and minimum length, L=4 (See FIG. 9A). Most of the motifs are located in the β-strands in the core of the protein. All residues known to be involved in metal ion binding of APE1, including 68N, 96E, 210D, 212N, 308D, and 309H are part of the twelve motifs. The three PROSITE motifs (Falquet, et al., 2002, The PROSITE database, its status in 2002, *Nucleic Acids Res.*, 30, 235-238) defined for APE correspond to the motifs 2, 9, 10 and 11 defined by the present invention.

Figure 11:
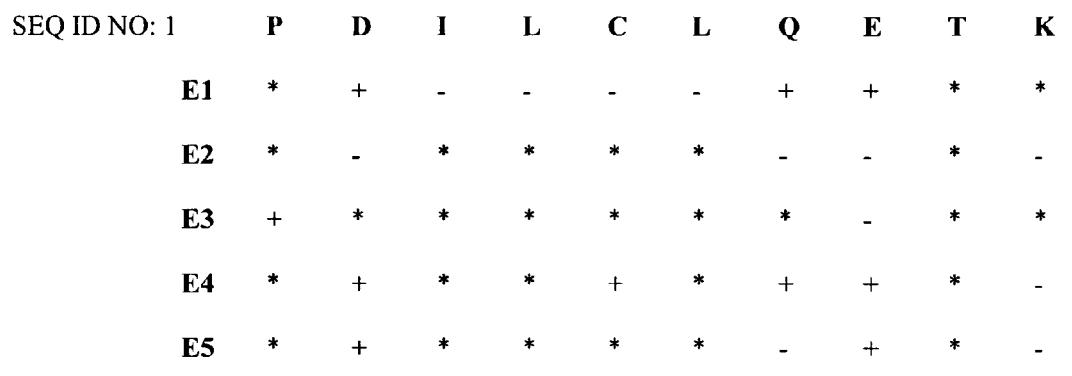

FIG. 11 shows a qualitative description of a motif, where + or − indicates significant components at the given position with the average values and * means an insignificant component.

With respect to FIG. 9A, the 12 motifs of the APE family identified according to the present invention, were used as query sequences to locate the best scoring windows in the sequences of human APE (1 hd7.pdb; S1), *E. coli* exonuclease (1ako.pdb; S2), bovine Dnase I (2dnj.pdb, S3) and the IPPP domain of synaptojanin from yeast (1i9y.pdb, S4). These S values are compared to the distribution of values for the highest scoring window over all sequences in the APE family belonging to APE and in the ASTRAL40 database. The * indicates structurally equivalent motifs, based on FSSP/DALI alignments for the four PDB files.

The 12 Motifs are Differentially Conserved in the APE Family

Figure 14:
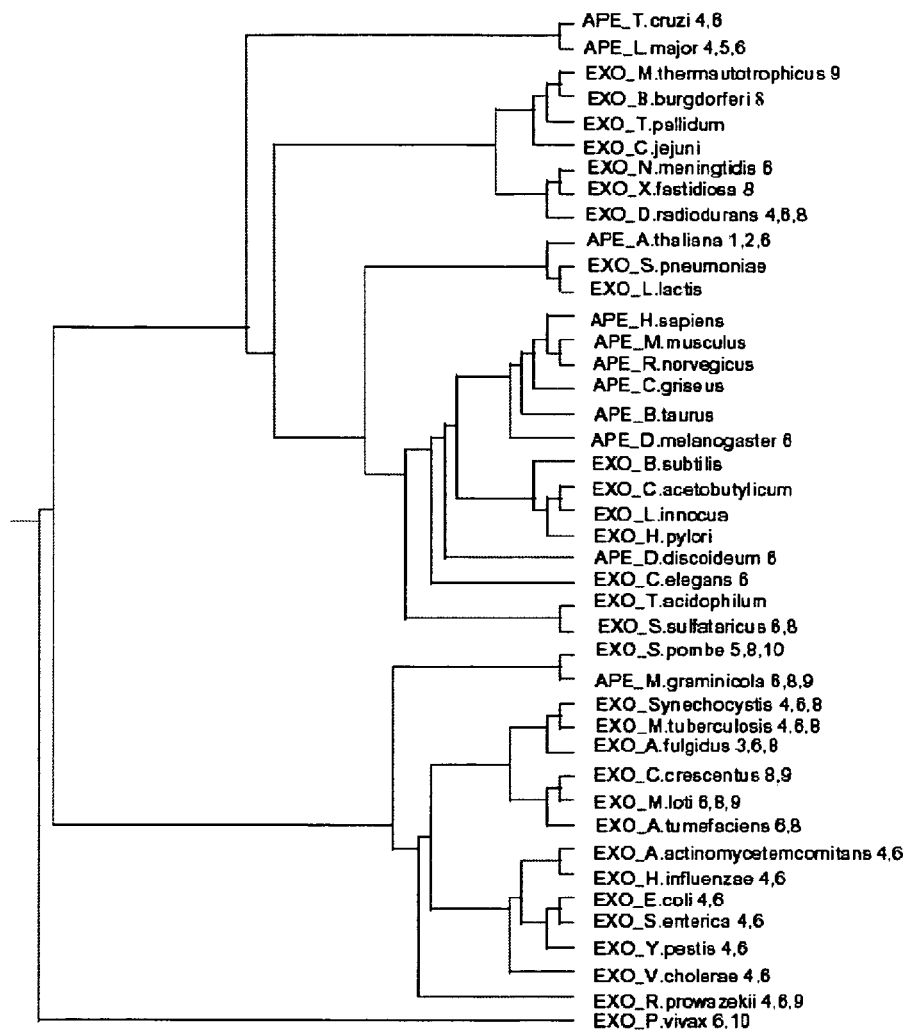
FIG. 14 shows a dendrogram of 42 different apurinic/apyrimidinic endonucleases and exonucleases used for the multiple alignment of the APE family for use in describing one example of the use of an analysis process according to the present invention. Number(s) indicate motif(s) that did not receive a significantly high score by subjecting the individual sequence of the protein to the motif search.

Scanning the individual APE sequences with the motif profiles identifies most of the motifs in an equivalent position as in the multiple sequence alignment. Motifs 1, 2, 7, 11 and 12 are particularly well conserved and have consistently high score (S) values. However, motifs 4, 6 and 10 score lower in enteric pathogenic bacteria such as *H. influenza*, *E. coli*, *S. enterica*, *Y. pestis* and *V. cholerae*, which might be related to the observed differences in the activity compared to eukaryotes (Schein, et al., 2002) (see dendrogram of the APE family in FIG. 14). FIG. 14 shows a dendrogram of 42 different apuinic/apyrimidinic endonucleases and exonucleases used for the multiple alignment of the APE family. Number(s) indicate motif(s) that failed to score the highest among competing scores from the rest of the scanning windows.

Distribution of Scores in ASTRAL40

FIGS. 12A-12L compares distribution of the highest scores for all motifs in each of the 3635 sequences in the ASTRAL40 database (solid line) to the target scores in the APE family (dashed line). Both distributions can be approximated as a Gaussian function. The scores for motifs 1, 2, 3, 5, 7, 11 and 12, most specific to the APE family, are clearly distinguished.

Ranking all proteins in ASTRAL40 according to the overall score for APE similarity, it was found that all the known members of the DNase-like superfamily at the top of the ranking (See FIG. 9B). The Figure indicates that close homologues should have an overall score greater than about 0.5. All sequences with scores between 0.35 and 0.5 were either phosphatases and/or contained a metal ion binding site. Two of the proteins (1MDA and 1EKM) have catalytic centers containing Cu(II), one has 2 $Zn^{2+}$ ions (1QQ9), and another contains Fe(II) (1MPY).

FIG. 9B shows a table of the APE related sequences in the ASTRAL40 database. Motifs that scored higher than their average scores in the database were considered as hits and the sequences were ranked according to the bit score obtained for all motif hits.

Identification of APE Protein Family and Superfamily using Molegos

If a 3D structure is known for one or more proteins in the aligned sequences or protein family, the sequence and 3D structural motifs can be combined to find related proteins (Schein, et al., 2002). Structurally related motifs, or molegos, were defined as those segments with a fractional window score greater than 0.6 and a RMSD value less than 2.5 Å for C atoms (See FIG. 9C). As with the scoring method based only on sequence, the higher ranking sequences with scores >0.5 were known members of the DNase-I/APE/IPP superfamily. Six proteins with no overall structural or sequence similarity to this superfamily had scores between 0.3 and 0.5. Of these, three contained one (1D09) or two $Zn^{2+}$ (1QQ9) and 1ATL) ions in their active site, one (1D2N) contained $Mg^{2+}$, and one $Ca^{2+}$.

FIG. 9C shows a table of the APE related sequences in the ASTRAL40 database. Motifs scoring with a fractional window score greater than 0.6 and RMSD less than or equal to 2.5 Å were considered to be molegos. Sequences were ranked according to the bit score obtained for all molego hits. Metal ions present in the protein structures are indicated in brackets.

PSI-BLAST and BLOCKS Search for APE Family and DNase-I Superfamily Members

Identification of members of a superfamily using the currently available sequence profile methods is difficult. For example, PSI-BLAST (a trade designation for a tool used) searching, using a local program or NCBI web-based version with default parameters (E-value 0.005), detected members of the APE family in the non-redundant sequence database. However, neither version revealed DNase-I or IPP sequences even after several iterations. When the E-value was increased to 0.1, synaptojanin was revealed within the first iterations, but bovine DNase-I was only detected after 4 iterations, along with more than 500 additional entries. PSI-BLAST (a trade designation for a tool used) also failed to recognize DNase-I or synaptojanin in the ASTRAL40 database, even when we added APE sequences to allow it to form a profile. The BLOCKS a trade designation for a tool used) search engine did not recognize homology to DNase-I even when the E-value cutoff was extended to 100. In contrast, our method identified these proteins clearly in the structural database (see FIGS. 9B and 9C).

Identifying and Using PCP Motifs and Molegos

A search method has been developed to locate elements with similar physical-chemical motifs in distantly related proteins. It is demonstrated that the PCP motifs generated by the present invention from a multiple alignment of APE sequences correlated well with motifs identified by other methods, and our database search method efficiently located known homologues. Our Bayesian scoring method discriminated members of the DNase-I superfamily from the bulk of sequences in the representative ASTRAL40 database (see FIG. 9B). Further, it is shown that combining sequence and structural data effectively discriminates proteins, with no overall similarity that shares partial function (metal binding) with the APE family.

$E^1$-$E^5$ Vectors Provide an Alternative Scoring Method for Evaluating Homology All the commonly used methods for genome sequence searching rely on similar, statistically derived scoring matrices (Altschul, et al., 1997, Gapped BLAST and PSI-BLAST: a new generation of protein database search programs, *Nucleic Acids Res.*, 25, 3389-3402; Kostich, et al., 2002, Human members of the eukaryotic protein kinase family, *Genome Biology*, 3, 43). Frequently, the same scoring matrix is used to search for related sequences (for example, with a tool available under the trademark of BLAST), prepare a multiple alignment to analyze sequence conservation and to locate distant relatives of the family according to motif conservation. According to, Venkatarajan, et al., 2001, New quantitative descriptors of amino acids based on multidimensional scaling of a large number of physical-chemical properties, *J. Mol. Model.*, 7, 445-453, the five property vectors represent all known physical-chemical properties, and provide an alternative to using the amino acid alphabet (Rigoutsos, et al., 2002, Dictionary-driven protein annotation, *Nucleic Acids Res.*, 30, 3901-3916) or selected physical-chemical properties (Dubchak, et al., 1999, Recognition of a protein fold in the context of the SCOP classification, *Proteins*, 35, 401-407) to identify homology. Our PCP motifs complement existing methods for functional cross networking of protein families (Marcotte, et al., 1999, A combined algorithm for genome-wide prediction of protein function, *Nature*, 402, 83-86; Marcotte, E. M., 2000, Computational genetics: finding protein function by nonhomology methods, *Curr. Opin. Struct. Biol.*, 10, 359-365; Overbeek, et al., 1999, The use of gene clusters to infer functional coupling, *Proc. Natl Acad. Sci. USA*, 96, 2896-2901).

Shared PCP Motifs and Molegos Identify DNase-I Superfamily Members

Despite their low overall sequence identity, APE, DNase-I and IPP families share a similar 3D structure and are members of a superfamily with a common SCOP designation (Lo Conte, et al., 2002, SCOP database in 2002: refinements accommodate structural genomics, *Nucleic Acids Res.*, 30, 264-267). The present invention rapidly identified members of this superfamily based on their shared PCP motifs. The most conserved motifs, 1, 2, 7 and 12, were found in structurally equivalent regions as defined by FSSP/DALI (Holm, et al., 1996, Mapping the protein universe, *Science*, 273, 595-602) in an alignment for the DNase-I superfamily members. The structurally equivalent motifs, or molegos, identified by our program are boxed in the FSSP alignment of DNase-I superfamily in FIG. 13. These motifs dictate the formation of a β-strand core that serves as the supporting architecture for metal ion binding and phosphorolysis by members of the APE/DNase-I/IPP superfamily (Schein, et al., 2002). No non-APE protein sequence in the ASTRAL40 database scored higher than the average total score ($S_x$) of 1772 bits calculated for the 42 APE sequences. Thus the present invention is highly sensitive and specific for detecting APE related sequences.

Proteins with Highest Scores Relative to APE Bind Metal Ions

A high proportion of metal ion binding proteins were found as the highest scoring proteins by searching for proteins that have similar sequences and 3D structure motifs (See FIG. 9C). FIG. 9C indicates that all of the highest scoring proteins identified in the ASTRAL40 structural database, that is those that contained molegos most similar to those of the APE superfamily, use metal ion based catalysis.

This result demonstrates that a new automated method for identifying protein motifs that are conserved according to physical-chemical properties in aligned sequences is provided. PCP profiles of these motifs can be used to locate distantly related proteins in sequence database. The 12 motifs identified according to the methods of the present invention in the APE family include the signatures in the PROSITE database and all amino acids shown previously to be essential for function. The motif profiles successfully identified likely homologues of APE in a database, including several with no overall sequence or structural similarity. Further, combining sequence and structural data to locate proteins that share functional similarities has also been shown.

All references cited herein are incorporated in their entirety as if each were incorporated separately. This invention has been described with reference to illustrative embodiments and is not meant to be construed in a limiting sense. For example, when the term column is used herein, a column could be row if a translation of other terms in accordance therewith is performed. This is the same for other terms, such as, vertical, horizontal or any other directional element. These terms are used to simplify the understanding of the present invention and not to be unduly limiting on the scope of the present invention. Various modifications of the illustrative embodiments, as well as additional embodiments of the invention, will be apparent to persons skilled in the art upon reference to this description.

What is claimed is:

1. A method for use in sequence data analysis comprising:

providing a multiple sequence alignment of a plurality of sequences, wherein the multiple sequence alignment comprises a column of aligned amino acids and/or gaps for each horizontal position of the multiple sequence alignment;

providing a plurality of numerical physical-chemical property (PCP) descriptors for each amino acid based on a plurality of physical-chemical properties thereof, wherein each of the plurality of numerical PCP descriptors corresponds to one of "N" eigenvectors used in defining the amino acids in terms of physical-chemical properties;

describing each amino acid in the multiple sequence alignment quantitatively in terms of the plurality of PCP descriptors as a series of "N" eigenvectors resulting in "N" PCP described sequence alignments, wherein each PCP described sequence alignment corresponds to and is defined with numerical PCP descriptors which correspond to one of the "N" eigenvectors, and further wherein each PCP described sequence alignment comprises a plurality of columns corresponding to the columns of the multiple sequence alignment;

analyzing each of the PCP described sequence alignments, on a column by column basis, to generate conservation property data for each column, wherein the conservation property data for each column comprises an average value for the numerical PCP descriptors in the column and a standard deviation associated with the average value, and a relative entropy value for the column;

analyzing the conservation property data for each of the PCP described sequence alignments to detect consecutive horizontal positions of the multiple sequence alignment where the physical-chemical properties are conserved based on at least the relative entropy determined for each column;

defining one or more PCP motifs in the multiple sequence alignment based at least on the detection of consecutive horizontal positions of the multiple sequence alignment where the physical-chemical properties are conserved according to at least one eigenvector; and outputting one or more of the defined PCP motifs to at least one of a user, a display, and a file user readable format.

2. The method of claim 1, wherein analyzing the conservation property data for each of the PCP described sequence alignments comprises analyzing the conservation property data for each of the PCP described sequence alignments to detect consecutive horizontal positions where the relative entropy satisfies a predetermined limit.

3. The method of claim 1, wherein defining one or more PCP motifs in the multiple sequence alignment further comprises using user specified gap and minimum length limits to define the one or more PCP motifs, wherein each PCP motif comprises a plurality of consecutive horizontal positions in the multiple sequence alignment.

4. The method of claim 1, further wherein the method comprises using the one or more defined PCP motifs to search a sequence database resulting in identification of one or more related sequence segments having PCP characteristics similar to one or more of the defined PCP motifs for output to at least one of a user, a display, and a file in user readable format.

5. The method of claim 4, wherein each PCP motif comprises a plurality of consecutive horizontal positions in the multiple sequence alignment, wherein using the one or more PCP motifs to search a sequence database for related sequence segments comprises defining each of the PCP motifs as a series of PCP motif profile matrices, wherein each PCP motif profile matrix of the series corresponds to one of the "N" eigenvectors, and further wherein values for each PCP motif profile matrix comprise an average value of the numerical PCP descriptors in the column at each horizontal position of the PCP motif and a standard deviation associated with the average value, and a relative entropy value for each horizontal position of the PCP motif.

6. The method of claim 5, wherein using the one or more PCP motifs to search a sequence database for related sequence segments comprises:
   converting each of one or more sequences of the sequence database to a searchable form using the numerical PCP descriptors;
   using a positional scoring function to match values of the series of PCP motif profile matrices defined for each PCP motif to segments of each of the searchable matrices resulting in scored segments; and
   selecting at least one scored segment for each of the searchable matrices as being a best match to each PCP motif based on results of the positional scoring function.

7. The method of claim 6, wherein each of the selected scored segments forms a part of one of a plurality of proteins of the sequence database, and wherein the method further comprises ranking the plurality of proteins according to which protein has PCP characteristics that are the closest to the plurality of sequences used to provide the multiple sequence alignment.

8. The method of claim 7, wherein ranking the plurality of proteins comprises ranking one or more of the plurality of proteins based on application of a Bayesian scoring function.

9. The method of claim 7, wherein ranking the plurality of proteins further comprises ranking one or more of the plurality of proteins based on structural similarity.

10. The method of claim 7, wherein ranking the plurality of proteins comprises:
    determining an overall PCP similarity distance score associated with each of the one or more proteins of the sequence database; and
    ranking the one or more proteins of the sequence database based on the overall PCP similarity scores for the proteins and relative to what a random score for the proteins would be.

11. The method of claim 6, wherein each of the selected scored segments forms a part of one of a plurality of proteins of the sequence database, and wherein the method further comprises:
    providing structural data for the one or more selected sequence segments;
    providing query structural data related to the PCP motifs;
    calculating segmental root mean square deviation between the query structural data and the structural data for the one or more selected sequence segments; and
    ranking the one or more proteins of the sequence database based on the calculated segmental root mean square deviation.

12. A computer program for use in conjunction with a processing apparatus to analyze sequence data, wherein the computer program is operable when used with the processing apparatus to:
    recognize a multiple sequence alignment of a plurality of sequences, wherein the multiple sequence alignment comprises a column of aligned amino acids and/or gaps for each horizontal position of the multiple sequence alignment;
    recognize a plurality of numerical physical-chemical property (PCP) descriptors for each amino acid based on a plurality of physical-chemical properties thereof, wherein each of the plurality of numerical PCP descriptors corresponds to one of "N" eigenvectors used in defining the amino acids in terms of physical-chemical properties;
    describe each amino acid in the multiple sequence alignment quantitatively in terms of the plurality of PCP descriptors as a series of "N" eigenvectors resulting in "N" PCP described sequence alignments, wherein each PCP described sequence alignment corresponds to and is defined with numerical PCP descriptors which correspond to one of the "N" eigenvectors, and further wherein each PCP described sequence alignment comprises a plurality of columns corresponding to the columns of the multiple sequence alignment;
    analyze each of the PCP described sequence alignments, on a column by column basis, to generate conservation property data for each column, wherein the conservation property data for each column comprises an average value for the numerical PCP descriptors in the column and a standard deviation associated with the average value, and a relative entropy value for the column;
    analyze the conservation property data for each of the PCP described sequence alignments to detect consecutive horizontal positions of the multiple sequence alignment where the physical-chemical properties are conserved based on at least the relative entropy determined for each column; and
    define one or more PCP motifs in the multiple sequence alignment based at least on the detection of consecutive horizontal positions of the multiple sequence alignment where the physical-chemical properties are conserved according to at least one eigenvector, wherein the one or more defined PCP motifs are output to at least one of a user, a display, and a file in user readable format.

13. The computer program of claim 12, wherein the computer program is operable when used with the processing apparatus to analyze the conservation property data for each of the PCP described sequence alignments by analyzing the conservation property data for each of the PCP described sequence alignments to detect consecutive horizontal positions where the relative entropy satisfies a predetermined limit.

14. The computer program of claim 12, wherein the computer program is operable when used with the processing apparatus to define one or more PCP motifs in the multiple sequence alignment using user specified gap and minimum length limits to define the one or more PCP motifs, wherein each PCP motif comprises a plurality of consecutive horizontal positions in the multiple sequence alignment.

15. The computer program of claim 12, wherein the computer program is further operable when used with the processing apparatus to use the one or more PCP motifs to search a sequence database for related sequence segments having PCP characteristics similar to one or more of the PCP motifs.

16. The computer program of claim 15, wherein each PCP motif comprises a plurality of consecutive horizontal positions in the multiple sequence alignment, and wherein the computer program is further operable when used with the processing apparatus to define each of the PCP motifs as a series of PCP motif profile matrices, wherein each PCP motif profile matrix of the series corresponds to one of the "N"

eigenvectors, and further wherein values for each PCP motif profile matrix comprise an average value of the numerical PCP descriptors in the column at each horizontal position of the PCP motif and a standard deviation associated with the average value, and a relative entropy value for each horizontal position of the PCP motif.

17. The computer program of claim 16, wherein the computer program is further operable when used with the processing apparatus to:
   convert each of one or more sequences of the sequence database to a searchable form using the numerical PCP descriptors;
   use a positional scoring function to match values of the series of PCP motif profile matrices defined for each PCP motif to segments of each of the searchable matrices resulting in scored segments; and
   select at least one scored segment for each of the searchable matrices as being a best match to each PCP motif based on results of the positional scoring function.

18. The computer program of claim 17, wherein each of the selected scored segments forms a part of one of a plurality of proteins of the sequence database, and wherein the computer program is further operable when used with the processing apparatus to rank one or more of the plurality of proteins according to which protein has PCP characteristics that are the closest to the plurality of sequences used to provide the multiple sequence alignment.

19. The computer program of claim 18, wherein the computer program is operable when used with the processing apparatus to rank one or more of the plurality of proteins based on application of a Bayesian scoring function.

20. The computer program of claim 18, wherein the computer program is operable when used with the processing apparatus to rank one or more of the plurality of proteins based on structural similarity.

21. The computer program of claim 18, wherein the computer program is operable when used with the processing apparatus to:
   determine an overall PCP similarity distance score associated with each of the one or more proteins of the sequence database; and
   rank the one or more proteins of the sequence database based on the overall PCP similarity scores for the proteins and relative to what a random score for the proteins would be.

22. The computer program of claim 17, wherein each of the selected scored segments forms a part of one of a plurality of proteins of the sequence database, and wherein the computer program is operable when used with the processing apparatus to:
   recognize structural data for the one or more selected sequence segments;
   recognize query structural data related to the PCP motifs;
   calculate segmental root mean square deviation between the query structural data and the structural data for the one or more selected sequence segments; and
   rank the one or more proteins of the sequence database based on the calculated segmental root mean square deviation.

* * * * *

SEQUENCE LISTING

<160> NUMBER OF SEQ ID NOS: 5

<210> SEQ ID NO 1
<211> LENGTH: 10
<212> TYPE: PRT
<213> ORGANISM: ARTIFICIAL SEQUENCE
<220> FEATURE:
<223> OTHER INFORMATION: MEMBER OF DNase-I SUPERFAMILY

<400> SEQUENCE: 1

Pro Asp Ile Leu Cys Leu Gln Glu Thr Lys
1               5                   10

<210> SEQ ID NO 2
<211> LENGTH: 275
<212> TYPE: PRT
<213> ORGANISM: ARTIFICIAL SEQUENCE
<220> FEATURE:
<223> OTHER INFORMATION: MEMBER OF DNase-I SUPERFAMILY

<400> SEQUENCE: 2

Leu Tyr Glu Asp Pro Pro Asp Gln Lys Thr Ser Pro Ser Gly Lys Pro
1               5                   10                  15

Ala Thr Leu Lys Ile Cys Ser Trp Asn Val Asp Gly Leu Arg Ala Trp
            20                  25                  30

Ile Lys Lys Lys Gly Leu Asp Trp Val Lys Glu Glu Ala Pro Asp Ile
        35                  40                  45

Leu Cys Leu Gln Glu Thr Lys Cys Ser Glu Asn Lys Leu Pro Ala Glu
    50                  55                  60

Leu Gln Glu Leu Pro Gly Leu Ser His Gln Tyr Trp Ser Ala Pro Ser
65                  70                  75                  80

Asp Lys Glu Gly Tyr Ser Gly Val Gly Leu Leu Ser Arg Gln Cys Pro
                85                  90                  95

Leu Lys Val Ser Tyr Gly Ile Gly Asp Glu Glu His Asp Gln Glu Gly
            100                 105                 110

Arg Val Ile Val Ala Glu Phe Asp Ser Phe Val Leu Val Thr Ala Tyr
        115                 120                 125

Val Pro Asn Ala Gly Arg Gly Leu Val Arg Leu Glu Tyr Arg Gln Arg
    130                 135                 140

Trp Asp Glu Ala Phe Arg Lys Phe Leu Lys Gly Leu Ala Ser Arg Lys
145                 150                 155                 160

Pro Leu Val Leu Cys Gly Asp Leu Asn Val Ala His Glu Glu Ile Asp
                165                 170                 175

Leu Arg Asn Pro Lys Gly Asn Lys Lys Asn Ala Gly Phe Thr Pro Gln
            180                 185                 190

Glu Arg Gln Gly Phe Gly Glu Leu Leu Gln Ala Val Pro Leu Ala Asp
        195                 200                 205

Ser Phe Arg His Leu Tyr Pro Asn Thr Pro Tyr Ala Tyr Thr Phe Trp
    210                 215                 220

Thr Tyr Met Met Asn Ala Arg Ser Lys Asn Val Gly Trp Arg Leu Asp
225                 230                 235                 240

Tyr Phe Leu Leu Ser His Ser Leu Leu Pro Ala Leu Cys Asp Ser Lys
                245                 250                 255

Ile Arg Ser Lys Ala Leu Gly Ser Asp His Cys Pro Ile Thr Leu Tyr
            260                 265                 270

Leu Ala Leu

-continued

275

<210> SEQ ID NO 3
<211> LENGTH: 268
<212> TYPE: PRT
<213> ORGANISM: ARTIFICIAL SEQUENCE
<220> FEATURE:
<223> OTHER INFORMATION: MEMBER OF DNase-I SUPERFAMILY

<400> SEQUENCE: 3

```
Met Lys Phe Val Ser Phe Asn Ile Asn Gly Leu Arg Ala Arg Pro His
 1               5                  10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 4
<211> LENGTH: 258
<212> TYPE: PRT
<213> ORGANISM: ARTIFICIAL SEQUENCE
<220> FEATURE:
<223> OTHER INFORMATION: MEMBER OF DNase-I SUPERFAMILY

<400> SEQUENCE: 4

```
Leu Lys Ile Ala Ala Phe Asn Ile Arg Thr Phe Gly Glu Thr Lys Met
 1               5                  10                  15

Ser Asn Ala Thr Leu Ala Ser Tyr Ile Val Arg Ile Val Arg Arg Tyr
            20                  25                  30
```

```
Asp Ile Val Leu Ile Gln Glu Val Arg Asp Ser His Leu Val Ala Val
            35                  40                  45

Gly Lys Leu Leu Asp Tyr Leu Asn Gln Asp Pro Asn Thr Tyr His
     50                  55                  60

Tyr Val Val Ser Glu Pro Leu Gly Arg Asn Ser Tyr Lys Glu Arg Tyr
65                  70                  75                  80

Leu Phe Leu Phe Arg Pro Asn Lys Val Ser Val Leu Asp Thr Tyr Gln
                85                  90                  95

Tyr Asp Asp Gly Cys Cys Gly Asn Asp Ser Phe Ser Arg Glu Pro Ala
                100                 105                 110

Val Val Lys Phe Ser Ser His Ser Thr Lys Val Lys Glu Phe Ala Ile
                115                 120                 125

Val Ala Leu His Ser Ala Pro Ser Asp Ala Val Ala Glu Ile Asn Ser
                130                 135                 140

Leu Tyr Asp Val Tyr Leu Asp Val Gln Gln Lys Trp His Leu Asn Asp
145                 150                 155                 160

Val Met Leu Met Gly Asp Phe Asn Ala Asp Cys Ser Tyr Val Thr Ser
                165                 170                 175

Ser Gln Trp Ser Ser Ile Arg Leu Arg Thr Ser Ser Thr Phe Gln Trp
                180                 185                 190

Leu Ile Pro Asp Ser Ala Asp Thr Thr Ala Thr Ser Thr Asn Cys Ala
                195                 200                 205

Tyr Asp Arg Ile Val Val Ala Gly Ser Leu Leu Gln Ser Ser Val Val
                210                 215                 220

Pro Gly Ser Ala Ala Pro Phe Asp Phe Gln Ala Ala Tyr Gly Leu Ser
225                 230                 235                 240

Asn Glu Met Ala Leu Ala Ile Ser Asp His Tyr Pro Val Glu Val Thr
                245                 250                 255

Leu Thr

<210> SEQ ID NO 5
<211> LENGTH: 336
<212> TYPE: PRT
<213> ORGANISM: ARTIFICIAL SEQUENCE
<220> FEATURE:
<223> OTHER INFORMATION: MEMBER OF DNase-I SUPERFAMILY

<400> SEQUENCE: 5

Tyr Asp Pro Ile His Glu Tyr Val Asn His Glu Leu Arg Lys Arg Glu
1               5                   10                  15

Asn Glu Phe Ser Glu His Lys Asn Val Lys Ile Phe Val Ala Ser Tyr
                20                  25                  30

Asn Leu Asn Gly Cys Ser Ala Thr Thr Lys Leu Glu Asn Trp Leu Phe
            35                  40                  45

Pro Glu Asn Thr Pro Leu Ala Asp Ile Tyr Val Val Gly Phe Gln Glu
     50                  55                  60

Ile Val Gln Leu Thr Ser Ala Asp Pro Ala Lys Arg Arg Glu Trp Glu
65                  70                  75                  80

Ser Cys Val Lys Arg Leu Leu Asn Gly Lys Cys Thr Ser Gly Pro Gly
                85                  90                  95

Tyr Val Gln Leu Arg Ser Gly Gln Leu Val Gly Thr Ala Leu Met Ile
                100                 105                 110

Phe Cys Lys Glu Ser Cys Leu Pro Ser Ile Lys Asn Val Glu Gly Thr
                115                 120                 125

Val Lys Lys Thr Gly Leu Gly Asn Lys Gly Ala Val Ala Ile Arg Phe
```

-continued

```
                130                 135                 140
Asp Tyr Glu Asp Thr Gly Leu Cys Phe Ile Thr Ser His Leu Ala Ala
145                 150                 155                 160

Gly Tyr Thr Asn Tyr Asp Glu Arg Asp His Asp Tyr Arg Thr Ile Ala
                165                 170                 175

Ser Gly Leu Arg Phe Arg Arg Gly Arg Ser Ile Phe Asn His Asp Tyr
                180                 185                 190

Val Val Trp Phe Gly Asp Phe Asn Tyr Arg Ile Ser Leu Thr Tyr Glu
            195                 200                 205

Glu Val Val Pro Cys Ile Ala Gln Gly Lys Leu Ser Tyr Leu Phe Glu
    210                 215                 220

Tyr Asp Gln Leu Asn Lys Gln Met Leu Thr Gly Lys Val Phe Pro Phe
225                 230                 235                 240

Phe Ser Glu Leu Pro Ile Thr Phe Pro Pro Thr Tyr Lys Phe Asp Ile
                245                 250                 255

Gly Thr Asp Ile Tyr Asp Thr Ser Asp Lys His Arg Val Pro Ala Trp
                260                 265                 270

Thr Asp Arg Ile Leu Tyr Arg Gly Glu Leu Val Pro His Ser Tyr Gln
            275                 280                 285

Ser Val Pro Leu Tyr Tyr Ser Asp His Arg Pro Ile Tyr Ala Thr Tyr
        290                 295                 300

Glu Ala Asn Ile Val Lys Val Asp Arg Glu Lys Lys Lys Ile Leu Phe
305                 310                 315                 320

Glu Glu Leu Tyr Asn Gln Arg Lys Gln Glu Val Arg Asp Ala Ser Gln
                325                 330                 335
```